US010438244B2

(12) United States Patent
Nelson et al.

(10) Patent No.: US 10,438,244 B2
(45) Date of Patent: Oct. 8, 2019

(54) INTEGRATED CONSUMER GENOMIC SERVICES

(71) Applicant: Illumina, Inc., San Diego, CA (US)

(72) Inventors: Nicholas A. Nelson, Encinitas, CA (US); Alexander G. Dickinson, San Diego, CA (US); Kenneth R. Bloom, San Diego, CA (US); Sophie I. Coon, San Diego, CA (US); Kenneth J. Sherman, Encinitas, CA (US); Kenneth G. Yocum, Encinitas, CA (US); Kevin P. Rhodes, San Diego, CA (US); Jerome O. Chadel, Encinitas, CA (US); Matthew L. Posard, Rancho Santa Fe, CA (US)

(73) Assignee: Illumina, Inc., San Diego, CA (US)

( * ) Notice: Subject to any disclaimer, the term of this patent is extended or adjusted under 35 U.S.C. 154(b) by 1000 days.

(21) Appl. No.: 14/621,036

(22) Filed: Feb. 12, 2015

(65) Prior Publication Data
US 2015/0227697 A1  Aug. 13, 2015

Related U.S. Application Data

(60) Provisional application No. 62/031,556, filed on Jul. 31, 2014, provisional application No. 61/939,695, filed on Feb. 13, 2014.

(51) Int. Cl.
*G16H 10/60* (2018.01)
*G06Q 30/02* (2012.01)
(Continued)

(52) U.S. Cl.
CPC ....... *G06Q 30/0269* (2013.01); *G06F 3/0486* (2013.01); *G16B 50/00* (2019.02); *G16H 10/60* (2018.01); *G16H 40/63* (2018.01)

(58) Field of Classification Search
CPC .... G06Q 30/0269; G16H 10/60; G16H 40/63; G06F 3/0486; G06F 19/28
See application file for complete search history.

(56) References Cited

U.S. PATENT DOCUMENTS 6,263,330 B1  7/2001  Bessette
7,401,026 B2  7/2008  Holden
(Continued)

FOREIGN PATENT DOCUMENTS

CN       1744080 A    3/2006
CN     102122326 A    7/2011
(Continued)

OTHER PUBLICATIONS

Angiuoli, Samuel V. et al., "Resources and Costs for Microbial Sequence Analysis Evaluated Using Virtual Machines and Cloud Computing", PLOS One, vol. 6, No. 10, Oct. 19, 2011, e26624-e26624.9.
(Continued)

*Primary Examiner* — Jonathan Durant
*Assistant Examiner* — Chad A Newton
(74) *Attorney, Agent, or Firm* — Illumina, Inc.

(57) ABSTRACT

The present invention provides a novel approach for consumer-driven interaction with sequencing data or genomic information. Sequencing data access, for users with a variety of access and permissions, may be mediated by a central hub. The hub may also facilitate access to the sequencing data for third party software applications. The hub may also provide data analysis or may have access to analyzed data to use such data in providing a user interface for a genome owner or for non-owner secondary users of the system.

17 Claims, 12 Drawing Sheets

(51) Int. Cl.
*G06F 3/0486* (2013.01)
*G16H 40/63* (2018.01)
*G16B 50/00* (2019.01)

(56) References Cited

U.S. PATENT DOCUMENTS

| | | | |
|---|---|---|---|
| 7,577,683 | B2 | 8/2009 | Cho et al. |
| 7,742,932 | B2 | 6/2010 | Segal |
| 7,869,956 | B2 | 1/2011 | Hoffman |
| 7,983,848 | B2 | 7/2011 | Hoffman et al. |
| 8,051,382 | B1 | 11/2011 | Kingdom et al. |
| 8,107,693 | B2 | 1/2012 | Osborne et al. |
| 8,239,216 | B2 | 8/2012 | Mccallie, Jr. et al. |
| 8,275,737 | B2 | 9/2012 | Kupershmidt et al. |
| 8,311,849 | B2 | 11/2012 | Soto et al. |
| 8,340,950 | B2 | 12/2012 | Avey |
| 8,364,665 | B2 | 1/2013 | Su et al. |
| 8,412,462 | B1 | 4/2013 | Ganeshalingam et al. |
| 8,417,459 | B2 | 4/2013 | Reese et al. |
| 2007/0061085 | A1 | 3/2007 | Fernandez |
| 2007/0150372 | A1* | 6/2007 | Schoenberg ........... G06Q 30/00 705/26.41 |
| 2008/0243551 | A1 | 10/2008 | Subramaniam |
| 2009/0049019 | A1 | 2/2009 | Su et al. |
| 2009/0222400 | A1 | 9/2009 | Kupershmidt et al. |
| 2009/0240441 | A1 | 9/2009 | Lapidus |
| 2010/0318528 | A1 | 12/2010 | Kupershmidt et al. |
| 2013/0096943 | A1 | 4/2013 | Carey et al. |
| 2013/0132392 | A1 | 5/2013 | Kenedy et al. |
| 2013/0166320 | A1 | 6/2013 | Kupershmidt et al. |
| 2013/0166599 | A1 | 6/2013 | Kupershmidt et al. |
| 2013/0275486 | A1 | 10/2013 | Dickinson et al. |
| 2014/0214579 | A1* | 7/2014 | Shen .................. G06F 19/28 705/26.1 |
| 2015/0120265 | A1* | 4/2015 | Amirav-Drory ........ G06F 19/26 703/11 |

FOREIGN PATENT DOCUMENTS

| | | |
|---|---|---|
| CN | 103389860 A | 11/2013 |
| CN | 103399948 A | 11/2013 |
| JP | 2001195367 A | 7/2001 |
| JP | 2004192210 A | 7/2004 |
| JP | 2010522943 A | 7/2010 |
| WO | 0131551 A1 | 5/2001 |
| WO | 2013/030827 A1 | 3/2013 |

OTHER PUBLICATIONS

Anonymous, "Drag and drop—Wikipedia, the free encyclopedia", XP855186887, Retrieved from the Internet: URL:http://en.wikipedia.org/w/index.php?title=Drag_and_drop&oldid=592127371 [retrieved on 2815-84-29], Jan. 24, 2014.

Ekanayake, et al., "Cloud Technologies for Bioniformatics Applications", IEEE Transactions on Parallel and Distributed Sytems, IEEE Service Center, vol. 22, No. 6, Jun. 1, 2011, 998-1011.

Oikawa, Marcio K. et al., "GenFlow: Generic flow for integration, management and analysis of molecular biology data", Genetics and Molecular Biology, vol. 27, No. 4, Dec. 1, 2004, 691-695.

Wall, et al., "Open Access Methodology Article Cloud Computing for Comparative Genomics", BMC Bioinformatics, Retrieved from the internet: http://www.biomedcentral.com/content/pdf/1471-2105-11-259.pdf [retrieved on Jun. 11, 2014], Jan. 1, 2010, 259.

"Drag and Drop", Wikipedia, the free encyclopediahttp://web.archive.org/web/20131207131429/http://en.wikipedia.org/wiki/Drag_and_drop, Sep. 23, 2013.

"International Search Report and Written Opinion for Application No. PCT/US15/15674", dated Aug. 20, 2015.

Yang, et al., "User Group Profile Modeling Based on User Transactional Data for Personalized Systems", Progress in Artificial Intelligence, vol. 3808 of the series Lecture Notes in Computer Science, Jan. 1, 2005, 337-347.

Office Action dated Apr. 11, 2018 from the Canadian Intellectual Property Office.

Korean Patent Office Notice of Preliminary Rejection dated Oct. 25, 2018 (with English translation).

CN Patent Application 201580019193.8, First Office Action dated Jan. 23, 2019.

Kitamura, Y., "Intelligent Information Integration Technologies on the Internet", 47th documents for Knowledge Base system Research JSAI(English abstract only), Mar. 27, 2000, 97-103.

Japanese Office Action with English translation, Application No. 2018-027661, mailed May 13, 2019.

* cited by examiner

INTEGRATED CONSUMER GENOMIC SERVICES

CROSS-REFERENCE TO RELATED APPLICATIONS

The present application claims the benefit of U.S. Provisional Application No. 61/939,695, entitled "INTEGRATED CONSUMER GENOMIC SERVICES" and filed Feb. 13, 2014, and U.S. Provisional Application No. 62/031,556, entitled "CONSUMER BIOLOGICAL DATA SYSTEM AND METHOD," filed Jul. 31, 2014, the disclosures of which are incorporated herein by reference for all purposes.

BACKGROUND

This disclosure relates generally to purchasing, distributing, sharing, displaying, and consuming genomic information, and more particularly, to purchasing, distributing, sharing, displaying, and consuming genomic information in a client server environment.

Traditionally, personal DNA or genome sequencing has been out of the reach of the general public. The machines needed to perform the sequencing were expensive, and usually purchased by larger entities, such as research institutions or corporations. Furthermore, these machines generally took long periods of time to sequence the DNA once a sample was obtained.

In recent years, the cost of sequencing and the time required to perform the sequence has decreased. Samples that previously required months to sequence can now be sequenced in a matter of days or weeks. Whole genome sequencing or partial genome sequencing can now be performed at a much lower cost, which removes the cost barrier for many consumers.

Several companies have taken advantage of the lower costs and shorter sequencing times to provide genomic products or services directly to individual consumers. For example, some companies offer services that allow an individual consumer to trace his or her ancestry based on a DNA sample. Other services include providing statistics based on the DNA sample, such as the likelihood the individual consumer will contract a specific disease within his or her lifetime.

However, after utilizing the services of these companies, the individual consumer, or user, will have to provide another DNA sample and wait for the sample to be sequenced if the user wanted to utilize the services of another company. For example, if a user had his DNA sequenced by a company that only traced ancestry, the user would have to have his DNA sequenced by another company if he wanted a report on the diseases he may contract in his lifetime. This can result in multiple companies performing duplicate work. This can also result in multiple copies of the user's DNA being stored in various locations, which may be difficult for the user to keep track of, and may also raise privacy concerns for a large number of consumers.

Further, such direct-to-consumer services may provide information in different formats that are difficult to reconcile with other types of available information, such as web-based search information. For example, certain consumers may have difficulty interpreting sequence data or statistical data without additional context or tools. Other consumers, such as medical professionals, may have little use for basic context information, but may instead wish to directly access raw genome data for further analysis. Accordingly, there is a need for consumer-driven interaction tools for various types of sequence data (e.g., genome data) and for more efficient purchasing, distributing, sharing, displaying, and consumption of genomic information.

SUMMARY

Provided herein are techniques for user interaction with sequencing data, genome data, or other types of biological data that may be mediated via a central hub that stores and controls access to various interactions with the sequencing data, either by the owner of the sequencing data or by secondary users of the system. For example, the interactions may include interactions with social media, data tools, consumer product offers, healthcare information, etc. These interactions may help a user push or pull information about the sequencing data from a user interface. In one example, a search engine may be provided that returns results based on genome information as well as a patient's permissions, which may be considered a "genome avatar" or "genome cookie" that is used for the patient's interaction with the system. For example, if a particular patient is interested in clinical trials but not marketing information, the results may skew towards the granted permissions. The consumer hub system addresses patient concerns about actionability and functionality in the genomic data provided by sequencing facilities.

In addition, sequencing or other biological data is memory-intensive. Accordingly, an end user may not wish to store such data on a mobile device or a tablet. However, because consumers use mobile devices more and more frequently to access the internet, having a remote hub that facilitates data access allows consumers to interact with their data without storing the data on their own devices. For example, a user may wish to use a novelty application that compares their genome to a celebrity genome. In such an embodiment, the user may download the application to their mobile device and grant permission for the application to access their genome data from the hub. Although genome comparison tools may require processing power beyond what a typical mobile device may be capable of, the analysis may be performed remotely (e.g., via the hub or a processor communicatively coupled to the hub), and the application may merely serve as an end recipient of a graphical output or other application display. In this manner, the genome data is not transmitted to and processed by the mobile device, which, as noted, frees up processing and memory.

The present techniques also provide granular and dynamic permission and/or access controls to the biological data. For example, sequencing data may include certain sequences that are associated with external states, including eye color, hair color, ethnicity, etc. In addition, certain types of sequence analysis, e.g., epigenetic data, may provide information about the age of the sequenced individual. Accordingly, an individual with personal sequencing data interacting with the hub as a consumer may wish to not only be anonymous, but also to block access to those sequences and/or data that may include identifying information. To facilitate the granular and dynamic permission controls, the present techniques may include user interface tools that guide a sequence owner through permission levels.

In certain embodiments, the present disclosure provides a system for sequencing data interaction. The system includes at least one server comprising one or more memory devices storing sequencing data associated with an owner. The server is coupled to a processor configured to execute instructions, which include receiving a first request from a first processor-based device to access the sequencing data;

accessing permission information for the sequencing data; providing instructions to the server to permit the first processor-based device to access the sequencing data when the permission information indicates that the first processor-based device is associated with the owner of the sequencing data; receiving a second request from a second processor-based device to access the sequencing data; and providing instructions to the server to permit the second processor-based device to access only a portion of the sequencing data when the permission information indicates that the second processor-based device is associated with an authorized user for limited genome access. In another embodiment, the processor is configured to execute instructions comprising: receiving a third request from a third processor-based device to access the sequencing data; and providing instructions to the server to permit the third processor-based device to access only default information about the sequencing data when the permission information indicates that the third processor-based device is not associated with an authorized user. In another embodiment, the first request from a first processor-based device to access the sequencing data comprises instructions for performing genome analysis of the genome on the server or other device remote from the first processor-based device and to transmit an output of the genome analysis to the first processor-based device. In another embodiment, the first request does not include a request to send the sequencing data to the first processor-based device. In another embodiment, the processor is configured to execute instructions comprising: receiving a third request from a third processor-based device associated with an outside user to access the sequencing data; and transmitting a notification to the first processor-based that an outside user request has been received to access the sequencing data.

In another embodiment, the present disclosure also provides a computer implemented method for interacting with sequence data. The method includes the steps of transmitting a search request to a server related to sequence data associated with an individual, wherein the sequence data is not stored on the mobile device; transmitting permission or identification information associated with the search request; receiving a search output comprising search engine results related to the sequence data based on the search request if a user associated with the search request has permission to access the sequence data based on the permission or identification information; and displaying the search output. In another embodiment, the processor is configured to execute instructions comprising: receiving an update to the permission information from the first processor-based device. The update may include instructions for allowing full or partial access to the genome information for the third-processor-based device or for allowing a full or partial access to the genome information in response to future requests from other outside users with similar profiles to the outside user associated with the third processor-based device, e.g., a clinical trial manager and wherein the update comprises instructions to accept requests for sequencing data access to other clinical trial managers. The update may include instructions for denying access to the genome information for the third processor-based device when the outside user is a retail vendor. Updates may include instructions to deny access to the genome information in response to future requests from other outside users with similar profiles to the outside user associated with the third processor-based device. In certain embodiments, the search output may include comprises search engine results for a clinical condition and wherein the search output is based on an analysis of the sequence data. The search engine results may be ranked or filtered based analysis of the sequence data. The analysis of the sequence data may include identification of one more mutations or polymorphisms associated with a clinical condition. The search output may include search engine results for genetic markers or pharmaceutical compounds (e.g., based on whether the sequence data includes sequences associated with variable pharmacogenetic responses for the pharmaceutical compound). In one embodiment, the method may include receiving a default search output not related to the sequence data if a user associated with the search request does not have permission to access the sequence data based on the permission or identification information.

In another embodiment, the present disclosure provides a system for storing sequence information. The system includes at least one networked computer system. The networked computer system is configured to store a plurality of sequences associated with respective sequence owners, wherein each respective sequence comprises one or more permissions; receive a request from a secondary user to access information related to sequences from the plurality of sequences associated with a particular common feature; determine which sequences of the plurality of sequences are associated with the particular common feature; and allow the secondary user access to only the information relating to the sequences associated with the particular common feature and permissions permitting the secondary user to access the information. In one embodiment, the at least one networked computer system is configured to transmit the information relating to the sequences associated with the particular common feature and permissions permitting the secondary user to access the information to the secondary user. The information may include contact or identification information, social media profile information, or sequence data. In one embodiment, the at least one networked computer system is configured to receive a new sequence associated with a new sequence owner; determine if the sequence is associated with the particular common feature; and notify the new sequence owner that there is an outstanding access request for the new sequence data because of the particular common feature In another embodiment, the present disclosure also provides a computer implemented consumer system for sequencing data. The system includes at least one processor configured to: receive sequence data and profile data associated with a sequence owner; analyze the sequence data; receive a request from the sequence owner to interact with the sequence data; determine a user interface configuration for the sequence owner interaction with the sequence data based on the analysis of the sequence data and the profile data; and transmit information related to the user interface configuration to a remote device associated with the sequence owner. The information related to the user interface configuration may include suggestions for joining one or more social media groups based on the sequence data or for installing one or more applications related to the sequence data.

In another embodiment, the present disclosure also provides a system for analyzing sequencing data. The system includes at least one processor configured to: receive sequence data associated with a sequence owner; receive privacy data associated with the sequence data; receive profile data associated with the sequence owner; receive a request from a secondary user to interact with the sequence data; determine a level of permitted access by the secondary user to the sequence data based on the privacy data; and transmit information related to the sequence data or the profile data to the secondary user based on the level of permitted access. The level of permitted access may be based on the type of secondary user or may be specific to only a portion of the sequence data.

In another embodiment, the present disclosure also provides a method for processing genomic information that includes: dragging, by a user, a genomic representation to a vendor representation in a graphical user interface; upon a pre-determined percentage of the genomic representation overlapping with the vendor representation, determining a vendor-defined dataset, wherein the vendor-defined dataset is defined by a vendor; comparing the vendor-defined data subset to a user-defined dataset; based on the comparison, determining if the vendor-defined dataset is a subset of the user-defined dataset; if the vendor-defined dataset is a subset of the user-defined dataset: displaying genomic offerings from the vendor in the graphical user interface; if the vendor-defined dataset is not a subset of the user-defined dataset: identifying the portions of the vendor-defined dataset that are not a subset of the user-defined dataset; and displaying, in the graphical user interface, the vendor-defined dataset that is not a subset of the user-defined dataset.

In another embodiment, the present disclosure also provides a system for processing genomic information that includes: a processor configured to: drag a genomic representation to a vendor representation in a graphical user interface; upon a pre-determined percentage of the genomic representation overlapping with the vendor representation, determine a vendor-defined dataset, wherein the vendor-defined dataset is defined by a vendor; compare the vendor-defined data subset to a user-defined dataset; based on the comparison, determine if the vendor-defined dataset is a subset of the user-defined dataset; if the vendor-defined dataset is a subset of the user-defined dataset: display genomic offerings from the vendor in the graphical user interface; if the vendor-defined dataset is not a subset of the user-defined dataset: identify the portions of the vendor-defined dataset that are not a subset of the user-defined dataset; and display, in the graphical user interface, the vendor-defined dataset that is not a subset of the user-defined dataset.

In another embodiment, the present disclosure also provides a method for processing genomic information that includes: storing a first user transaction data in a central repository, wherein the first user transaction data is created as the first user completes a first user transaction, wherein the first user transaction includes at least one from the following: view a vendor, view a vendor offering, and purchase a vendor offering; storing a second user transaction data in a central repository, wherein the second user transaction data is created as the second user completes a second user transaction, wherein the second user transaction includes at least one from the following: view a vendor, view a vendor offering, and purchase a vendor offering; comparing the first user transaction data to the second user transaction data; pushing a notification to the second user in a graphical user interface with a vendor offering based on the comparison.

In another embodiment, the present disclosure also provides a system for processing genomic information that includes: a processor configured to: store a first user transaction data in a central repository, wherein the first user transaction data is created as the first user completes a first user transaction, wherein the first user transaction includes at least one from the following: view a vendor, view a vendor offering, and purchase a vendor offering; store a second user transaction data in a central repository, wherein the second user transaction data is created as the second user completes a second user transaction, wherein the first user transaction includes at least one from the following: view a vendor, view a vendor offering, and purchase a vendor offering; compare the first user transaction data to the second user transaction data; push a notification to the second user in a graphical user interface with a vendor offering based on the comparison.

In another embodiment, the present disclosure also provides a method for processing genomic information that includes: prompting a user, through a graphical user interface, to select at least a portion of the user's genomic information; upon receiving the selection of at least a portion of the user's genomic information, prompting the user, through the graphical user interface, to indicate a level of sharing for the selection of at least a portion of the user's genomic information; and based on the selection of at least a portion of the user's genomic information and the indicated level of sharing, allowing a second user to view the user's genomic information.

In another embodiment, the present disclosure also provides a method for processing genomic information that includes: receiving a sequence of a user's DNA; receiving phenotype information of the user; associating the sequence of the user's DNA with the phenotype information of the user; storing the sequence of the user's DNA and the phenotype information of the user in a central repository; generating an icon in a graphical user interface by an application on a client device; and creating a pointer from the icon to the stored sequence of the user's DNA.

In another embodiment, the present disclosure also provides computer program product, the computer program product comprising machine readable instructions for: dragging, by a user, a genomic representation to a vendor representation in a graphical user interface; upon a pre-determined percentage of the genomic representation overlapping with the vendor representation, determining a vendor-defined dataset, wherein the vendor-defined dataset is defined by a vendor; comparing the vendor-defined data subset to a user-defined dataset; based on the comparison, determining if the vendor-defined dataset is a subset of the user-defined dataset; if the vendor-defined dataset is a subset of the user-defined dataset: displaying genomic offerings from the vendor in the graphical user interface; if the vendor-defined dataset is not a subset of the user-defined dataset: identifying the portions of the vendor-defined dataset that are not a subset of the user-defined dataset; and displaying, in the graphical user interface, the vendor-defined dataset that is not a subset of the user-defined dataset.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

As used herein the singular forms "a", "and", and "the" include plural referents unless the context clearly dictates otherwise. Thus, for example, reference to "a sequence" may include a plurality of such sequences, and so forth. All technical and scientific terms used herein have the same meaning as commonly understood to one of ordinary skill in the art to which this invention belongs unless clearly indicated otherwise.

Figure 1:
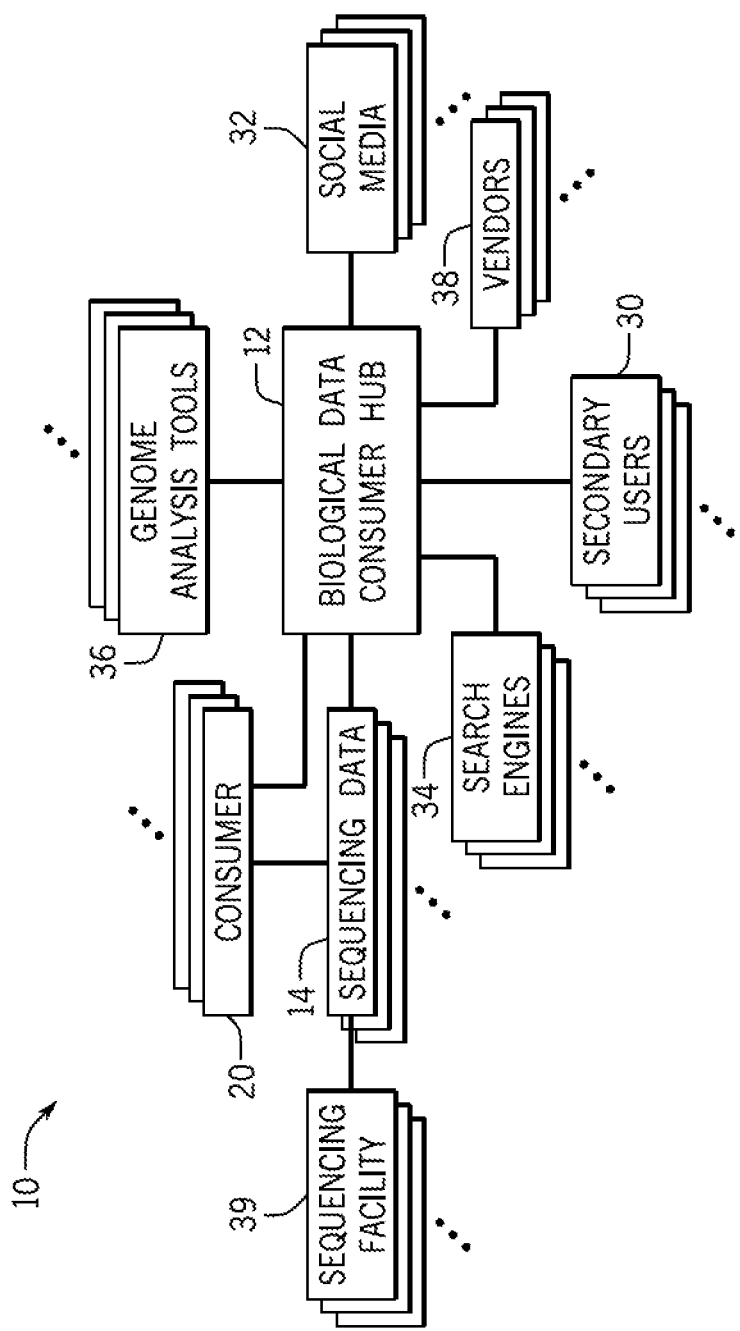
FIG. 1 is a diagrammatical overview for a system incorporating a biological data consumer hub in accordance with the present invention.

Turning now to the drawings, and referring first to FIG. 1, a biological data consumer hub system 10 is illustrated diagrammatically. The system 10 includes a biological data consumer hub 12 that serves as a clearinghouse to interconnect various users, services, functionality, and data. For example, in one embodiment, the hub 12 serves as a central storage for sequencing data 14 from a plurality of individual owners. In some embodiments, the sequencing data 14 is generated from or owned by consumers 20 in the system 10. That is, the sequencing data 14 is personal sequencing data. In other embodiments, the sequencing data 14 is owned by research institutions or corporate entities rather than individuals, and these institutions may also be considered consumers 14 in such embodiments.

For example, it should be understood that the sequencing data 14 may be generated from the consumer's own biological sample and, therefore, may represent all or part of the consumer's own genome. Accordingly, the consumer 20 may also be the owner of the sequencing data 14. In certain embodiments, the consumer 20 may own or control access to sequencing data 14 from biological samples that are not their own, e.g., family members or non-human data. For example, the sequencing data 14 may be generated from a non-human biological sample from companion animals (e.g., cats, dogs, birds), agricultural animals, plants, food cultures, laboratory samples, cultures taken (e.g., throat or wound swab) from a subject, etc. Further, the sequencing data 14 may represent all or only part of a genome sequence, and, further, may include genomic DNA, cDNA, hnRNA, mRNA, rRNA, tRNA, cRNA, alternatively spliced mRNA, small nucleolar RNA (snoRNA), microRNAs (miRNA), small interfering RNAs (siRNA), piwi RNAs (piRNA), any form of synthetic or modified RNA, fragmented nucleic acid, nucleic acid obtained from subcellular organelles such as mitochondria or chloroplasts, and nucleic acid obtained from microorganisms or DNA or RNA viruses that may be present on or in a biological sample. As used herein, "genome DNA" may refer to a full or partial genome, and a genome sequence may refer to a full or partial genome sequence. The sequencing data 14 may include germline sequences, somatic sequences, gene expression and transcriptome sequences, epigenetic analysis (e.g., methylation, acetylation, histone folding, structural variation such as chromatin mapping or protein-DNA interaction mapping), tissue sequences (e.g., tumor vs. normal). In addition, while embodiments of the present disclosure may be discussed in the context of sequencing data, it should be understood that the hub 12 may facilitate access to other types of biological data, such as protein sequence data, microarray data, etc. Accordingly, the hub 12 may be configured to store data including may represent a protein sequence, a nucleic acid sequence, a polysaccharide profile, etc.

In certain embodiments, the sequencing data 14 may not be owned by any individual. For example, sequencing data 14 from unclaimed (e.g., historical) or unowned biological samples may be of research interest. In such cases, the sequencing data 14 may be dedicated to the public or may be owned by the research institute or other entity that gathered the samples and arranged for the sequencing to occur. Further, it is envisioned that the hub 12 may also facilitate interaction with non-human sequencing data 14, including synthetic data, mammalian organism data (e.g., companion animals), eukaryotic organism data, prokaryotic organism data, virus data, etc. In certain embodiment, the sequencing data 14 may include microbial genomic data, such as data from environmental samples as well as microbial genomic data obtained from infected organisms (microbiome data) or human microbiome data.

In addition to facilitating access to sequencing data 14 for a consumer 20, the hub 12 may also facilitate access to the consumer's sequencing data 14 by secondary users 30. Such secondary users 30 may include medical providers, hospitals, insurance companies, and pharmaceutical companies. These secondary users 30 may have research or commercial interest in certain sequencing data 14. Further, the consumer 20 may also be a secondary user 30 when accessing data 14 not owned by him. For example, a consumer 20 may wish to access sequencing data from potential relatives for genealogical purposes. In such embodiments, the consumer 20 may be both a primary user and the secondary user 30.

Access to the data may also be requested by third party applications, such as social media applications 32, search engines 34, software applications (e.g., "apps") that may include various data analysis tools 36, and vendors 38, including consumer product vendors (e.g., shopping applications). For example, if a consumer is a member of a social media group for a specific disease (e.g., all members share a common sequence variant), the hub 12, operating under consumer-selected permissions, may allow access to the sequencing data 14 for that particular community. In other embodiments, social media applications may request access to the sequencing data 14 to aid in a birth parent search. In such an embodiment, a request to the hub 12 may involve a release of relevant portions of the sequencing data 14 that may aid in such a search. Other social media applications 32 or software applications 36 may include dating or behavioral groups. For example, a dating application may include a tool or function to assess the percentage match of the genomes of two users, an estimated "distance" between their genomes, or an estimated common ancestor (e.g., 4 generations, 5 generations) for two people. Such tools may perform the matches without providing the sequence data 14 to either user. That is, the applications 36 provide outputs based on the data, but not the data itself.

In the context of search engines 34, the sequencing data 14 may be provided as an input to relevant searches, as provided herein. Further, the sequencing data may also be used as inputs to data analysis tools 36, which may be part of add-on applications that a consumer 20 may wish to download. Such applications may be focused on providing medically relevant analysis, while other types of applications may be novelty applications that a consumer may buy via an application store. In such embodiments, the applications may interact with the sequencing data in a manner similar to a secondary user 30. For example, in one embodiment, an application request permission to access the sequencing data 14 of the consumer 20. Depending on the type of application, the permissions may be tailored to the analysis. For example, certain data analysis tools 36 may request location information as well as limited sequencing data 14. In this manner, a particular tool 36 may also link together with local social media, consumer retail product, or service applications 32.

The hub 12 may be configured to receive and store sequencing data 14, for example the hub 12 may receive sequencing data 14 from a sequencing facility 22. Alternatively or in addition, the hub 12 may facilitate access to sequencing data 14 stored remotely, e.g., stored at one or more sequencing facilities 22 or at a dedicated server facility. Further, the hub 12 may communicate with one or more servers that are part of a cloud computing environment to access sequencing data 14.

Figure 2:
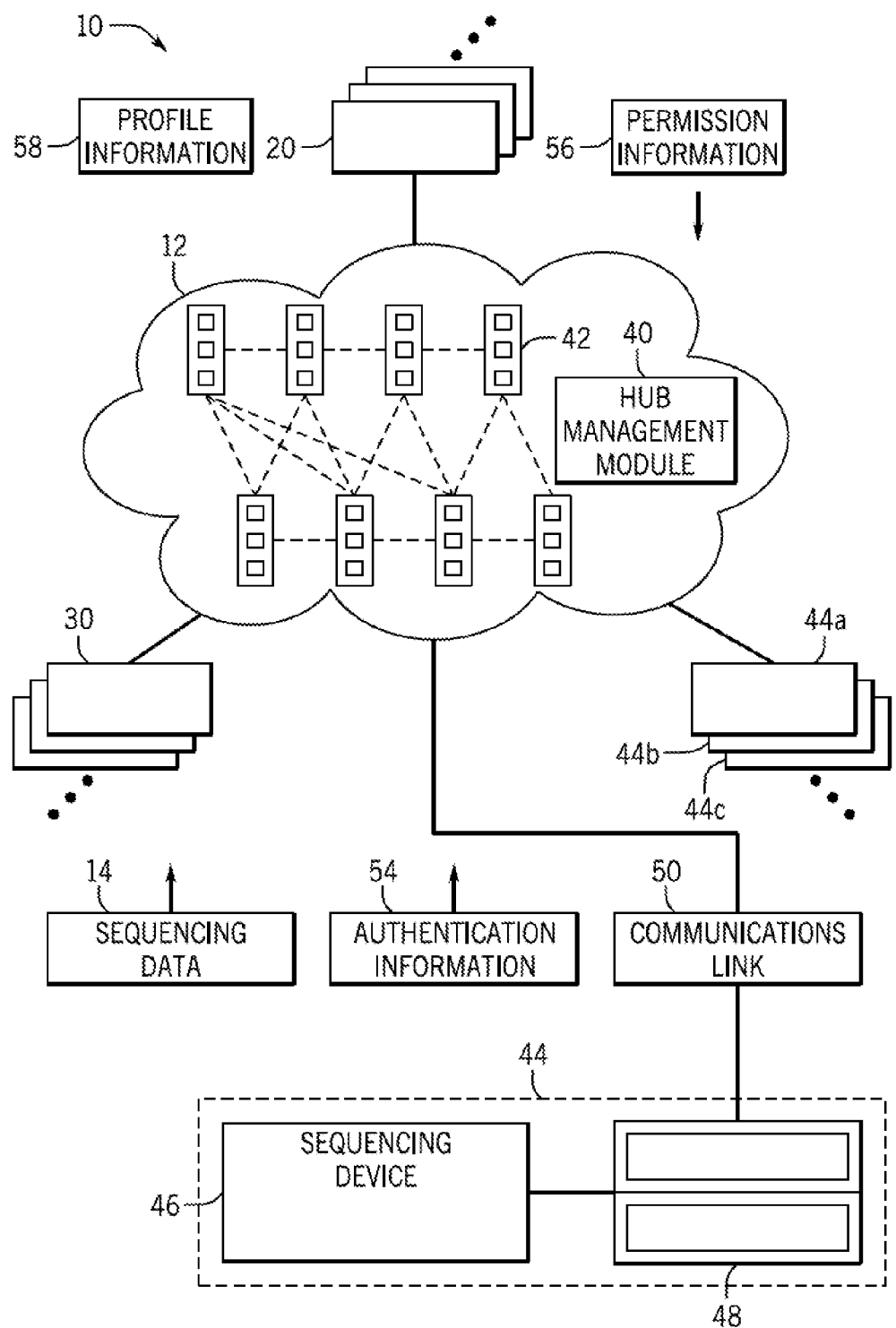
FIG. 2 is a diagrammatical overview for a system incorporating a hub as part of a networked computing environment in accordance with the present invention.

FIG. 2 is an example of a hub management module 40 and system that may be used in conjunction with the hub 12 of FIG. 1. In the depicted embodiment, certain features of the hub 12 may be implemented as part of a cloud computing environment that includes a plurality of distributed nodes 42. The computing resources of the nodes 42 are pooled to serve multiple consumers, with different physical and virtual resources dynamically assigned and reassigned according to consumer demand. Examples of resources include storage, processing, memory, network bandwidth, and virtual machines. The nodes 42 may communicate with one another to distribute resources, and such communication and management of distribution of resources may be controlled by a cloud management module 40, residing one or more nodes 42. The nodes 42 may communicate via any suitable arrangement and protocol. Further, the nodes 14 may include servers associated with one or more providers. For example, certain programs or software platforms may be accessed via a set of nodes 42 provided by the owner of the programs while other nodes 42 are provided by data storage companies. Certain nodes 42 may also be overflow nodes that are used during higher load times.

In one embodiment, the hub management module 40 is responsible for handling data communication with the participants in the system 10. The hub 12 is configured to communicate with various users, including users of devices for generating biological data. Such data may include sequence data generated via a sequencing device 44, which in particular embodiments may include a device 18 that includes a module to accept a biological sample and generate sequence data and an associated computer 20 that includes executable instructions for analyzing or communicating the sequence data to the hub 12. It should be understood that, in certain embodiments, the sequencing device 44 may also be implemented as an all-in-one device. The sequencing device 44 is configured to communicate with the hub 12 via a suitable communications link 50. The communication with the hub 12 for the sequencing device 44 as well as other hub users (e.g., consumers 20, secondary users 30) may include communication via a local area network (LAN), a general wide area network (WAN), and/or a public network (e.g., the Internet) via the communications link 50. In particular, the communications link 50 sends sequencing data 26 and, in certain embodiments, authentication information 54, to the hub 12. The authentication information may confirm that the sequencing device 44 is a client of the hub 12.

As noted, the hub 12 may serve multiple users or clients with associated devices, e.g., devices 44a, 44b, and 44c. Further, the hub 12 may also be accessed by other types of clients, such as secondary users 30 or third party software holders (see FIG. 1; e.g., search engines 34, vendors 38, etc.). Accordingly, the hub 12 may provide different types of services depending on the access level of the particular client. A sequencing client may have access to storage and data analysis services, while a secondary user 30 may have access only to shared or public sequences. Third party software holders 34 may negotiate with sequencing clients to determine appropriate access privileges. For example, open source software may be offered for free or on limited license basis, while other types of software may be offered according to various fee or subscription bases.

Once the sequencing data 14 has been communicated to the hub 12, further interaction with and access to the sequencing data 14 may not necessarily be coupled to the sequencing device 44. Such embodiments may be beneficial in embodiments in which the owner of the biological sample and/or sequence data has contracted for sequencing, e.g., to a core sequencing facility 39. In such embodiments, the primary user may be the owner (e.g., the consumer 20) while the core laboratory facility associated with the sequencing device 44 is at most a secondary user 30 after the sequencing data 14 has been communicated to the hub 12. Accordingly, the consumer 20 may also provide permission information 56 for further access to the sequencing data 14 for secondary users 20, which may be preset and communicated concurrently with the sequencing data 14 (via the sequencing device 44). Alternatively or additionally, the consumer 20 may also directly provide the permission information 56. The consumer 20 may also provide profile information 58 (e.g., health information, personal characteristics) that is associated with the sequencing data 14.

In certain embodiments, the sequence data may be accessed through security parameters such as a password-protected client account in the hub 12 or association with a particular institution or IP address. The sequencing data 14 may be accessed by downloading one or more files from the hub 12 or by logging into a web-based interface or software program that provides a graphical user display in which the sequence data is depicted as text, images, and/or hyperlinks. In such an embodiment, the sequencing data 14 may be provided to the consumer 20 or secondary user 30 in the form of data packets transmitted via a communications link or network.

As used herein, sequencing data 14 may refer to data obtained during a sequencing run, which refers to a repetitive process of physical or chemical steps that is carried out to obtain signals indicative of the order of monomers in a polymer. The signals can be indicative of an order of monomers at single monomer resolution or lower resolution. In particular embodiments, the steps can be initiated on a nucleic acid target and carried out to obtain signals indicative of the order of bases in the nucleic acid target. The process can be carried out to its typical completion, which is usually defined by the point at which signals from the process can no longer distinguish bases of the target with a reasonable level of certainty. If desired, completion can occur earlier, for example, once a desired amount of sequence information has been obtained. In some embodiments, a sequencing run is composed of several cycles, where each cycle includes a series of two or more steps, and the series of steps is repeated in each cycle. For example, a 10 cycles of a sequencing-by-synthesis run can be carried out to identify a sequence of 10 nucleotides. Each of the 10 cycles can include steps of polymerase catalyzed extension of a primer to add a nucleotide analog having a blocking moiety and label moiety; detecting the label moiety on the extended primer; and removing the label moiety and blocking moiety from the extended primer.

The sequencing run may be implemented via the sequencing device 44 according to any sequencing technique, such as those incorporating sequencing-by-synthesis methods described in U.S. Patent Publication Nos. 2007/0166705; 2006/0188901; 2006/0240439; 2006/0281109; 2005/0100900; U.S. Pat. No. 7,057,026; WO 05/065814; WO 06/064199; WO 07/010,251, the disclosures of which are incorporated herein by reference in their entireties. Alternatively, sequencing by ligation techniques may be used in the sequencing device 44. Such techniques use DNA ligase to incorporate oligonucleotides and identify the incorporation of such oligonucleotides and are described in U.S. Pat. Nos. 6,969,488; 6,172,218; and 6,306,597; the disclosures of which are incorporated herein by reference in their entireties. Some embodiments can utilize nanopore sequencing, whereby target nucleic acid strands, or nucleotides exonucleolytically removed from target nucleic acids, pass through a nanopore. As the target nucleic acids or nucleotides pass through the nanopore, each type of base can be identified by measuring fluctuations in the electrical conductance of the pore (U.S. Pat. No. 7,001,792; Soni & Meller, *Clin. Chem.* 53, 1996-2001 (2007); Healy, *Nanomed.* 2, 459-481 (2007); and Cockroft, et al. *J. Am. Chem. Soc.* 130, 818-820 (2008), the disclosures of which are incorporated herein by reference in their entireties). Yet other embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference in its entirety. Particular embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides, or with zero-mode waveguides as described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference in their entireties. Other suitable alternative techniques include, for example, fluorescent in situ sequencing (FISSEQ), and Massively Parallel Signature Sequencing (MPSS). In particular embodiments, the sequencing device 44 may be a HiSeq, MiSeq, or HiScanSQ from Illumina (La Jolla, Calif.).

The sequencing device 44 may generate sequencing data 14 as base call files. Both the sequencing device 44 and the hub 12 are capable of processing the base call files to perform Amplicon, de novo assembly, Library QC, metagenomics, resequencing, and smallRNA discovery. Other types of data analysis may include clinical analysis, such as GeneInsight. In particular embodiments, the data analysis may be performed according to industry or regulatory agency standards, such as CLIA. The files generated from the various analyses may take the form of FASTQ files, binary alignment files (bam) *.bcl, *.vcf, and/or *.csv files. The output files may be in formats that are compatible with available sequence data viewing, modification, annotation, and manipulation software. Accordingly, the accessible sequencing data 14 as provided herein may be in the form of raw data, partially processed or processed data, and/or data files compatible with particular software programs. Further, the output files may be compatible with other data sharing platforms or third party software.

Figure 3:
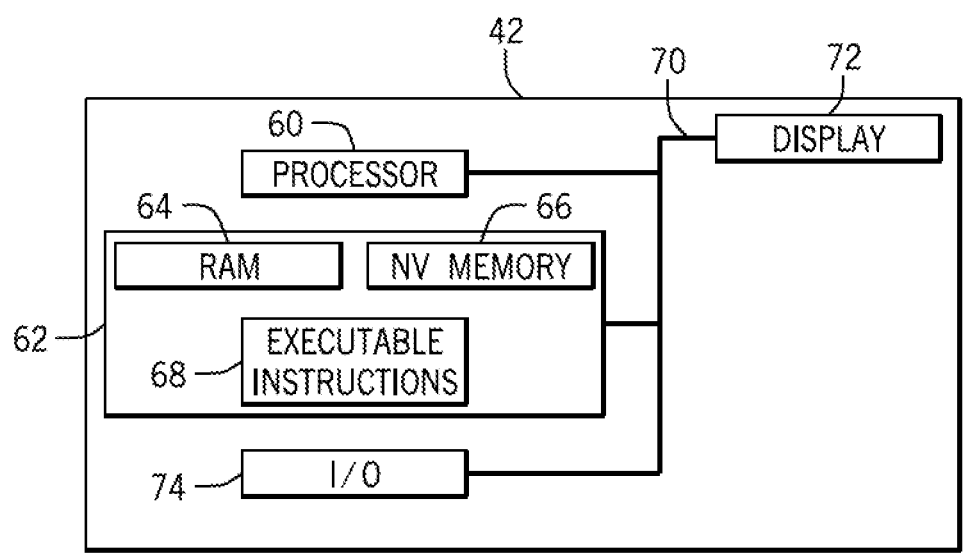
FIG. 3 is a diagrammatical overview of a control module of the hub of the type discussed with reference to FIG. 2.

FIG. 3 is a block diagram of the hub node 42. The hub node 42 may be implemented as one or more of a personal computer system, server computer system, thin client, thick client, hand-held or laptop device, multiprocessor system, microprocessor-based system, set top box, programmable consumer electronic, network PC, minicomputer system, mainframe computer system, or cloud computing environment that include any of the above systems or devices, and the like. Further, while the depicted embodiment is discussed in the context of the node 42, it should be understood that similar components may be implemented in devices used by the consumer 20 or secondary user 30 to interact with the hub 12 and/or the node 42. The node 42 may include one or more processors or processing units 60, a memory architecture 62 that may include RAM 64 and non-volatile memory 66. The memory architecture 62 may further include removable/non-removable, volatile/non-volatile computer system storage media. Further, the memory architecture 62 may include one or more readers for reading from and writing to a non-removable, non-volatile magnetic media, such as a hard drive, a magnetic disk drive for reading from and writing to a removable, non-volatile magnetic disk (e.g., a "floppy disk"), and/or an optical disk drive for reading from or writing to a removable, non-volatile optical disk such as a CD-ROM, DVD-ROM. The node 42 may also include a variety of computer system readable media. Such media may be any available media that is accessible by the cloud computing environment, such as volatile and non-volatile media, and removable and non-removable media.

The memory architecture 62 may include at least one program product having a set (e.g., at least one) of program modules implemented as executable instructions that are configured to carry out the functions of the present techniques. For example, executable instructions 68 may include an operating system, one or more application programs, other program modules, and program data. Generally, program modules may include routines, programs, objects, components, logic, data structures, and so on, that perform particular tasks or implement particular abstract data types. Program modules may carry out the functions and/or methodologies of the techniques as described herein including, but not limited to, primary sequence data analysis and secondary sequence analysis.

The components of the node 42 may be coupled by an internal bus 70 that may be implemented as one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The node 42 may also communicate with one or more external devices such as a keyboard, a pointing device, a display 72, etc.; that enable an operator to interact with the hub 12; and/or any devices (e.g., network card, modem, etc.) that enable node 42 to communicate with one or more other computing devices. Such communication can occur via I/O interfaces 74. Still yet, the nodes 42 of the hub 12 may communicate with one or more networks such as a local area network (LAN), a general wide area network (WAN), and/or a public network (e.g., the Internet) via a suitable network adapter.

The hub 12 may execute user interaction software (e.g., via a web-based interface or application platform) that provides a graphical user interface for users (e.g., consumers 20 and secondary users 30) and that facilitates access to sequence data 14, a community or group of researchers, data sharing or analysis programs, available third party software, and user selections for load balancing and instrument settings. For example, in particular embodiments, settings for a sequencing run on a sequencing device 44 may be set via the hub 12. Accordingly, the hub 12 and an individual sequencing device 44 (or consumer device/secondary user device) may be capable of two-way communication. Such an embodiment may be particularly useful for controlling parameters of a remote sequencing run.

As noted, the hub 12 may serve multiple users or clients with associated devices, e.g., devices 44a, 44b, and 44c. Further, the hub 12 may also be accessed by other types of clients, such as secondary users 30 or third party software holders (see FIG. 1; e.g., search engines 34, vendors 38, etc.). Accordingly, the hub 12 may provide different types of services depending on the access level and permissions 56 of the particular client. A sequencing client may have access to storage and data analysis services, while a secondary user 30 may have access only to shared or public sequences. Third party software holders may negotiate with consumers 20 to determine appropriate access privileges to the sequencing data 14.

Figure 4:
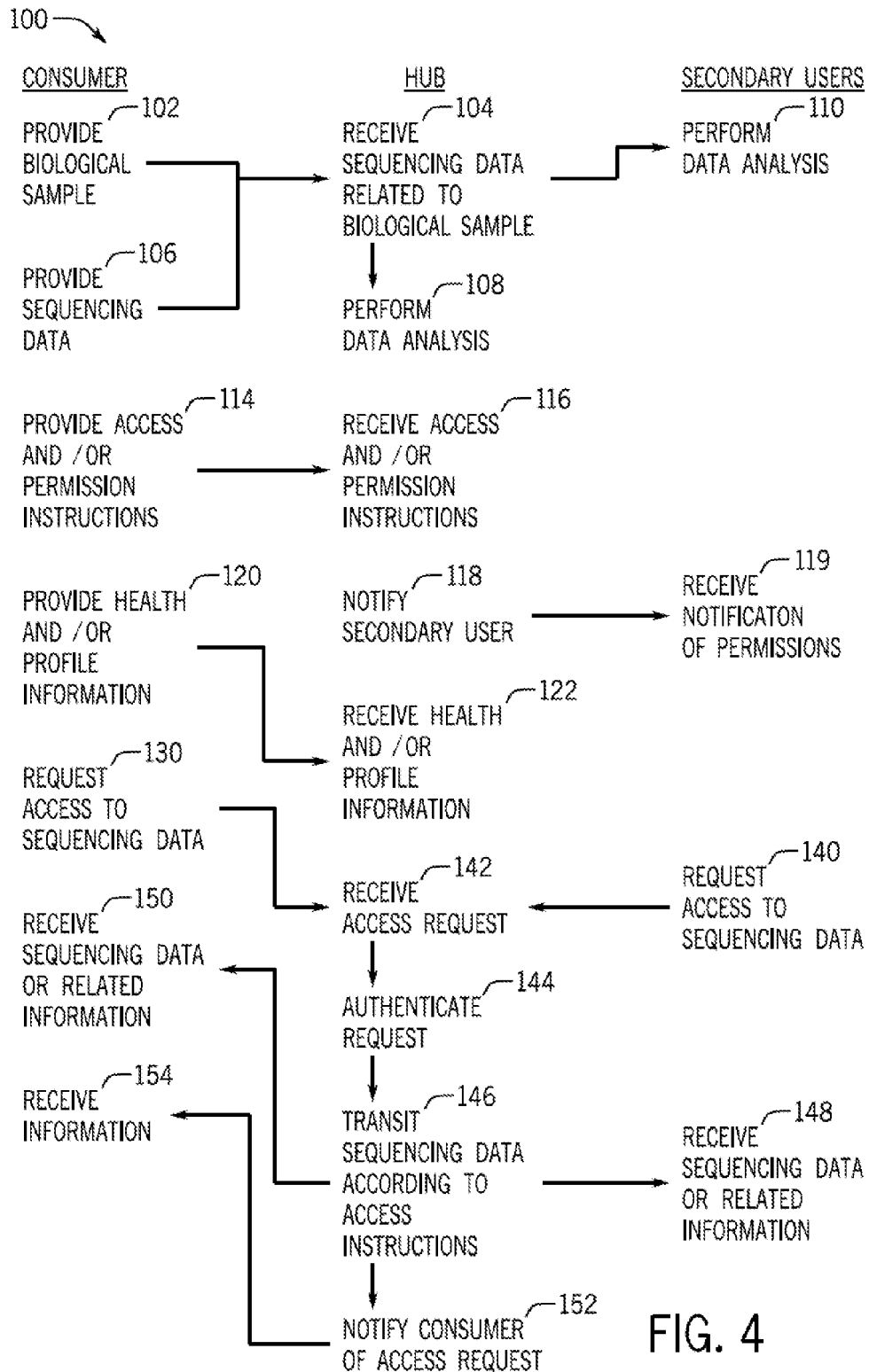
FIG. 4 is a flow diagram of a method of interaction between a primary user or consumer of sequencing data, the biological data consumer hub, and one or more secondary users that may be performed in conjunction with the system discussed with reference to FIG. 1.

As provided herein, the system 10 facilitates the interaction of consumers 20 and/or owners of sequencing data 14 with the hub 12 and collaborators or secondary users (e.g., secondary users 30). To that end, FIG. 4 is a flow diagram of the pathways of some exemplary interactions. The method 100 may encompass any viable subset or combination of the steps or interactions depicted. In one embodiment, the method 100 may begin with providing a biological sample at block 102. For example, the sample may be provided to the sequencing device 44, which in turn acquires sequencing data 14. When the sequence data 14 is acquired, the sequencing device 44 communicates the sequencing data 14 to the hub 12, which receives the sequence data at block 104. Alternatively, the consumer 20 may directly provide the data 14 at block 106.

The sequence data 14 in the hub 12 may be stored and/or further processed. For example, the hub 12 is capable of analyzing sequence data 14 (block 108) or providing instructions to a networked device to perform the analysis. A user may set parameters for data that are received by the hub 12. For example, the user may indicate which analyses are to be performed remotely, e.g., via the hub 12. In one embodiment, the parameters may be set such that primary analysis (e.g., base identification) is performed locally while secondary analysis (e.g., genome assembly) is performed in the hub 12. Alternatively, a secondary user 30 may be instructed or permitted to perform the data analysis (block 110). The results of the data analysis may be stored for later access by the consumer 20 and/or secondary user 30.

The system 10 also provides techniques for authorizing secondary users that include access and/or permission instructions that may be set by the user (block 114) and received at the sequencing device 44 (block 116). If the instructions indicate that the sequencing data 14 is to be shared with one or more secondary users 30, the instructions may be communicated by the hub 12 to notify the one or more secondary users 30 (block 118). The access is then implemented according to the instructions. For example, if the instructions include a notification provision, a notification is sent (block 118) to the secondary user, which may be received (block 119) in the form of an email or message in a cloud computing account, for example. The information provided by the consumer 20 may also include health and/or profile information (block 120). This information in turn is received at the hub 12 (block 122) and may be communicated to secondary users along with the sequencing data 14, as provided.

Access to the sequencing data 14 for the consumer may be facilitated by the hub 12 via a request by the consumer 20 (block 130). Upon receipt of the access request by the consumer 20 (block 142), the hub 12 authenticates the request (block 144) before transmitting the data 14 (block 146), which is received by the appropriate consumer-associated device (block 150). In other embodiments, the sequence data access instructions may also set permissions for at least partial access by a secondary user 30 who sends a request (block 140) to access the sequence data that is received by the hub 12 (block 142). The request is authenticated (block 144) based on the instructions at block 114 and the sequence data 14 is communicated according to the instructions at block 146. The secondary user 30 may access or receive the sequence data (block 148) in the form of a downloaded file or may access the sequence data via a web-based interface or a software package. When the secondary user 30 does not have permission to access the sequencing data 14, either a denial notice is provided or certain default profile information is provided. For example, a denial may include a message that "You do not have permission to access customer Joe P.'s sequence. Joe P. is male, age 29, from Wisconsin." Further, the hub 12 may notify the consumer 20 (block 152), which in turn receives the notification (block 154), that a secondary user has requested/accessed the sequencing data 14.

Figure 5:
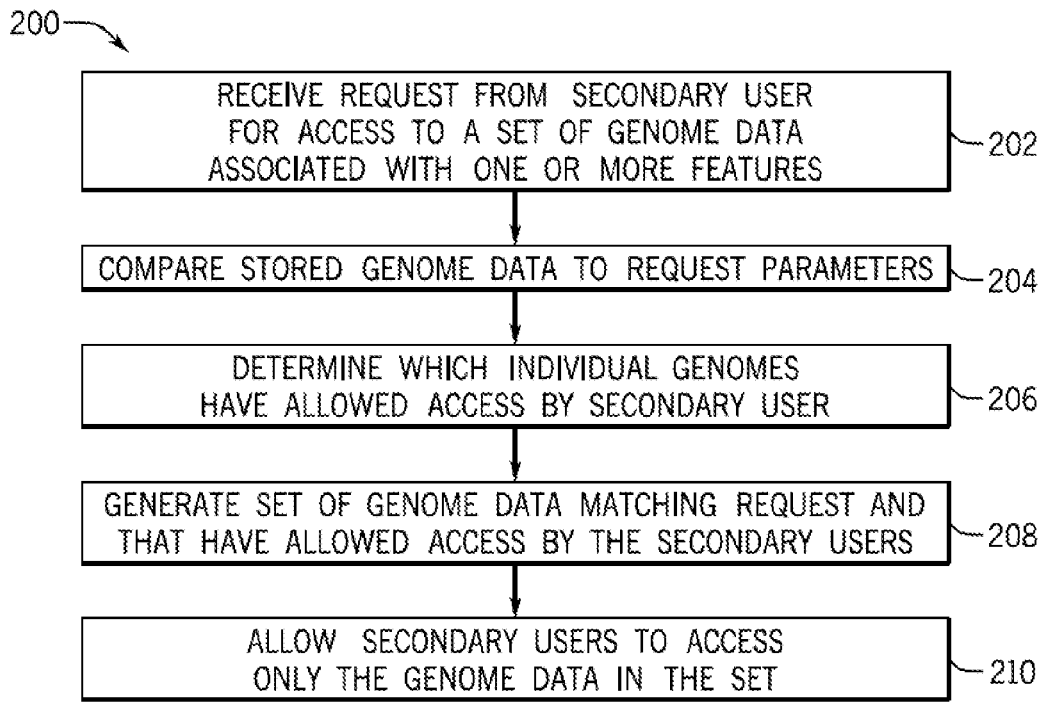
FIG. 5 is a flow diagram of a method of providing access to particular sequencing data to secondary users via the hub of the type discussed with reference to FIG. 1.

In addition to mediating intercommunication between individual consumers 20 and secondary users 30, the hub 12 may act as an intermediary for gathering information and/or data relating to groups of consumers and their sequence data 14. For example, FIG. 5 is a flow diagram for a method 200 of a gathering a set of genome data (e.g., sequencing data 14) with a particular common feature between them. At block 102, the hub 12 received a secondary user request for access to any genome data with a common feature of interest. The feature of interest may be the presence or absence of a particular sequence of interest, such as a gene or gene variant of interest, a gene mutation, an SNP, or a microsatellite sequence. In other embodiments, the particular common feature of interest may be related to the consumer profile information (e.g., profile information 58). For example, a secondary user 30 may be a clinical trial manager who is seeking participants in a particular age range, ethnicity, etc. Further, the clinical trial manager may be seeking participants with or without certain clinical profiles. On one embodiment, the profile may be cancer survivors who have been in remission for 3+ years. In such an embodiment, the clinical trial may be related to data mining of sequence data 14 from these individuals to look for beneficial sequences or beneficial epigenetic changes in the DNA. In one embodiment, the search may be a search for any open access sequences. That is, the search request may include only particular permissions settings as a search parameter. The hub 12 may compare the stored genome data and, if appropriate, profile information, to the request (block 204) to determine if there are any matching genome sequences.

While the hub 12 may store a set of genome sequence data 14 associated with consumers 20 matching the desired profile, not all of the stored sequences may be accessible to secondary users 30 based on the individual permissions settings of the sequence owners. At block 206, the hub 12 may determine which individual sequences have allowed access by the secondary user in question. Further, the permissions may be granular. That is, certain sequences may be open to all secondary users, other sequences may be open for all research but no commercial use. In other embodiments, certain sequences may be accessible only to one institution but not to other institutions of the same type. Accordingly, the set of sequences that match the search request and that have permissions granting the secondary user access (generated at block 208) may be smaller than the total set of matching sequences, regardless of permissions. At block 210, the hub 12 may permit the secondary user 30 to access the relevant genome data. Further, the hub 12 may initiate contact with the inaccessible members of the larger set to notify them of a request for access and indicate that the request was denied. In such an embodiment, the hub 12 may also receive updated privacy settings if the consumer 20 changes their privacy to allow access.

In another embodiment, the secondary user may wish to access not sequence data, but contact information for the consumer. That is, based on a sequence profile, the secondary user 30 may wish to market consumer products to a particular user. For example, if a consumer product company has determined that a sequence variant is associated with dandruff, the secondary user 30 may wish to market dandruff products to consumers with the variant. In other embodiments, the hub 12 may facilitate the contact with the consumers 20 to maintain consumer privacy.

The request may be structured as an ongoing search, such that, as new genome sequences are received by the hub 12, they are automatically assessed to determine if they include the feature of interest and appropriate permission settings. If so, the data is forwarded to the secondary user. If not, the consumer 20 may be notified that an outstanding request for their data is in place. In addition, as a consumer 20 interacts with the hub 12 for setup of genome information, the setup process may include automatic assessment for any outstanding requests for sequence data that their data and/or profile meet. In one embodiment, the requests are "pushed" onto the setup screen, and the consumer 20 may opt in or opt out as desired.

Figure 6:
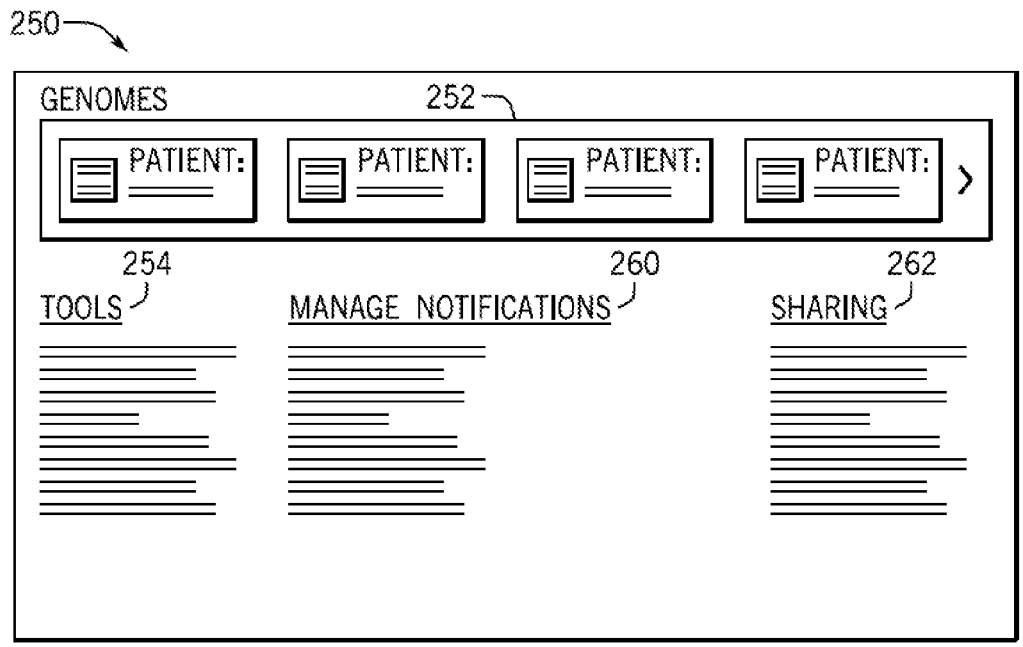
FIG. 6 is an example of a display screen of a user interface for secondary user access to sequencing data according to the flow diagram of FIG. 5.

For secondary users 30 who request genome or sequencing data 14 as part of being a member of the hub system 10, the hub 12 may provide a user interface for data interaction. Such services may be fee or subscription based, depending on the type of secondary user. FIG. 6 is an example of a graphical display screen 250 for interacting with the available sequence data 14. The graphical display screen 250 may include selectable menu options for selecting particular genomes and/or accessing data from the hub 12 related to the selected genomes. In addition, the displayed information may include links or linkable icons 254 for relevant data analysis applications or further information related to the depicted portion of the sequence data. The linkable icons 254 may be linked to relevant apps or applications. Clicking the link may take the user to an application store for data analysis or other tools from third party vendors. Because users will have a wide variety of data sets stored in the cloud, ranging in both size and the nature of their content, different application may be appropriate for different types of data sets. The display screen 250 may also display links for managing notification 260 and sharing 262.

Figure 7:
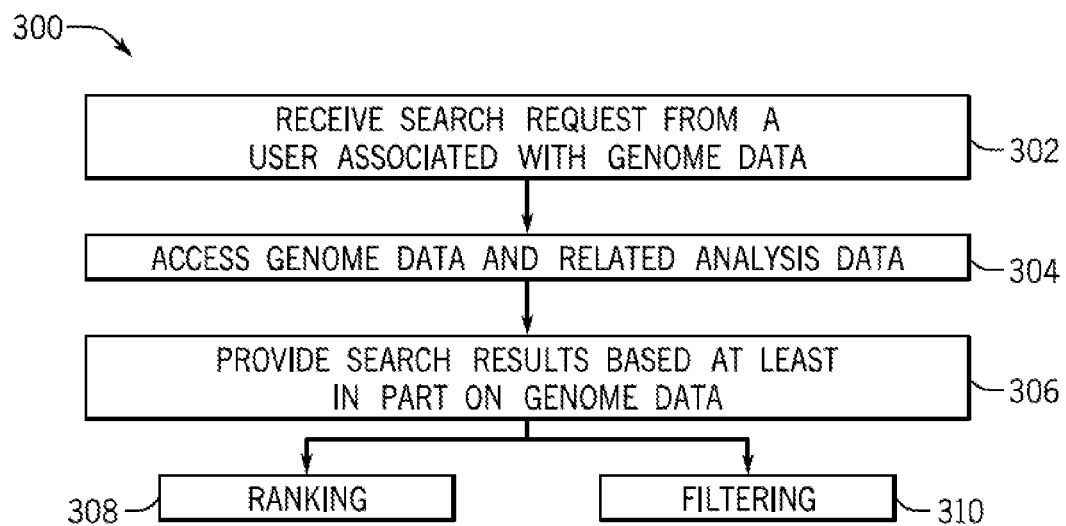
FIG. 7 is a flow diagram of a method of providing search results based on sequencing data via the hub of the type discussed with reference to FIG. 1.

In addition to mediating intercommunication between consumers 20 and secondary users 30, the hub 12 may act as an intermediary for software applications or other tools that may normally act in a sequence-independent manner. However in certain embodiments, providing the sequencing data 14 as an input to such tools may enhance or target particular outputs. For example, FIG. 7 is a flow diagram for a method of sequence-dependent searching that may be mediated by the hub 12. The consumer 20 or secondary user 30 may input search requests in a conventional manner, which are in turn received by the hub 12 (block 302). If the request is associated with any accessible sequence data 14, the sequence data and any related analysis data (e.g., the presence of particular mutations or variants) are accessed (block 304). The search results are provided to the requestor based on the accessed data (block 306). In certain embodiments, the search results are ranked (block 308) and/or filtered (block 310) based on the available sequence data.

In one embodiment, a search engine output may be ranked according to the sequence data 14. If the sequence data indicates that the consumer 20 has a particular variant associated with breast cancer, such as BRCA1, the search results for the term "breast cancer" may be ranked to include or weight BRCA1 as a term over other breast cancer results. This weighting is performed without any additional input from the consumer 20. In this manner, a consumer 20 does not need to be medically sophisticated in order to receive targeted search results. The hub 12 may include its own search engine, or the method 300 may serve an intermediary to conventional search engine results. For example, a Google search result for "breast cancer" may be submitted to the hub 12 and then ranked and/or filtered by the hub 12 according to the sequence data 14.

In another embodiment, the search engine output may be filtered to include or exclude certain results. For example, if the sequence data 14 indicates that the consumer 20 has a characteristic mutation in a CYP2D6 gene that is indicative of reduced codeine metabolism, their results for a search for "pain medication" may be filtered to exclude codeine. In another embodiment, the hub 12 may suggest particular search terms based on the sequence data 14. For example, if the sequence data 14 is part of an ancestry type of analysis, the search terms may include the predicted regions of origin for the consumer 20. Other types of searches may be ranked or filtered based on a predicted risk for developing a clinical condition as indicated by an analysis of the sequence data 14. Further, the search engine may be used to find doctors or practitioners that specialize in treating diseases associated with sequence mutations. In another embodiment, specific search results may be filtered based on ethnic origin as determined from the sequence data 14, e.g., based on variants that are or are not widely represented in particular ethnic groups. For example, certain ethnicities may have different likelihoods of developing particular clinical conditions. Accordingly, certain search results may be of higher interest (i.e., more likely clinical conditions) than others (i.e., less likely clinical conditions) relative to the general population or other ethnic groups.

Figure 8:
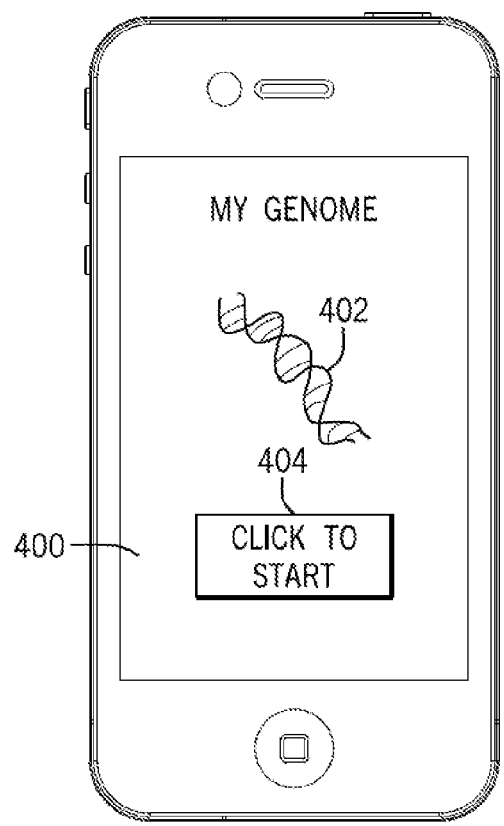
FIG. 8 is an example of a display screen of a user interface for interacting with owned sequencing data via the hub of the type discussed with reference to FIG. 1.
Figure 9:
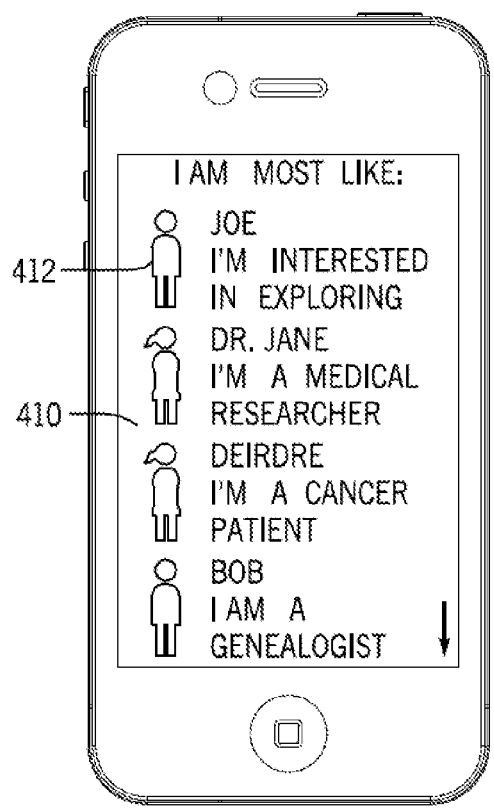
FIG. 9 is an example of a display screen of a user interface for setting up a user interface for interaction with owned sequencing data via the hub of the type discussed with reference to FIG. 1.
Figure 10:
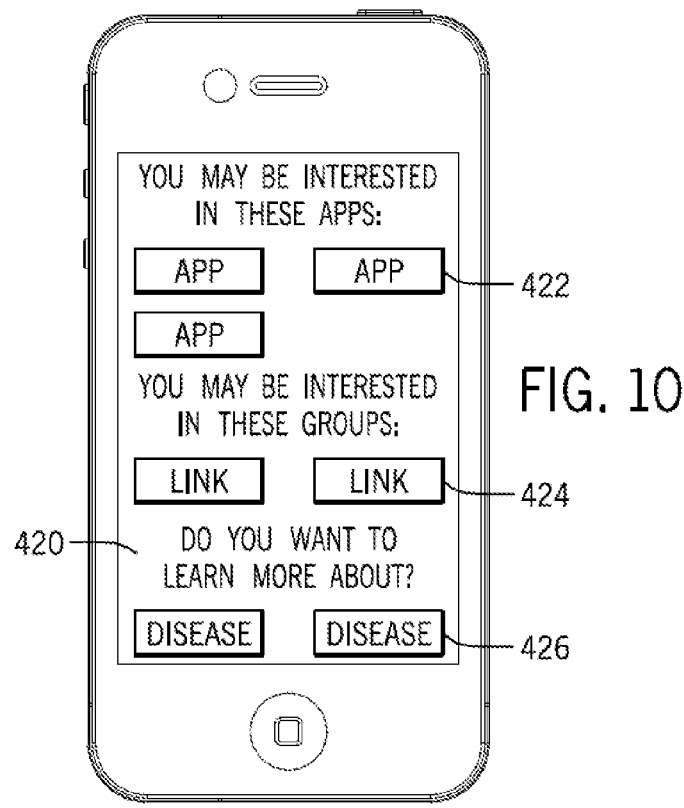
FIG. 10 is an example of a display screen of a user interface for setting up a user interface for interaction with owned sequencing data via the hub of the type discussed with reference to FIG. 1.

The hub 12 serves as a clearinghouse for sequence data 14 from multiple consumers 20 for the benefit of the consumers themselves as well as interested third parties. A consumer 20 may be medically sophisticated or naïve, and the hub 12 may be configured to create a customized user interface for a variety of different types of sequence data consumers. FIGS. 8-10 are examples of displayed graphical user interfaces that guide the consumer 20 through interaction with the sequence data 14 and the hub 12.

FIG. 8 is an example of a displayed introduction screen 400. The screen includes a genomic representation. For example, a person's whole or partial genome sequence (or other type of sequence data 14) may be represented by an icon 402 in an application window that is generated by an application in a client machine, such as a mobile phone. This icon 402, or genomic representation, may be used to identify the individual consumer or user to vendors that offer genomic services, such as genealogy. In some embodiments, the genomic representation itself holds the genomic information of the individual consumer. In some embodiments, the genomic representation may be an icon that points to data that is stored in a remote location, such as a server, or locally on the client machine, wherein the data include genomic information. This icon 402 may, in some embodiments, include genotype information, phenotype information, or a combination of genotype and phenotype information. Since the genomic representation and the genomic information that it includes may include private information, security measures, such as encryption, should be used wherever the genomic representation, or genomic information that the genomic representation points to, is stored, as well as the communication involving the genomic representation or genomic information. The introduction screen 400 may include a simplified soft key or link 404 to enter a more involved setup screen, as shown in FIG. 9

FIG. 9 is an example of a displayed setup screen 410 that allows a user to follow a default or automated setup according to a profile 412 that most fits their needs. By way of example, the profiles may include a relatively unsophisticated example user, "Joe," without any particular disease profile or interest area. Selecting one profile leads to the next associated setup screen, while selecting another profile leads to a different associated setup screen. Other profile examples include medical researchers, cancer patients, or genealogists. Each profile leads to a customized suggested setup, as shown in FIG. 10. The setup includes options for the consumer 20 to download suggested apps 422, join social media groups 424, and click on information about particular diseases 426. In other embodiments, the suggestion to join particular groups may be based on a sequence analysis and the presence of particular sequence variants. In another embodiment that may be appropriate for a consumer 20 with at least basic genetics knowledge, the consumer 20 may navigate a chromosome view of a genome, e.g., via scrolling and/or clicking. If a particular area is associated with analysis applications, sharing features, social media groups, news, and/or healthcare specialists, such options may be provided as a clickable link on the genome region.

Figure 11:
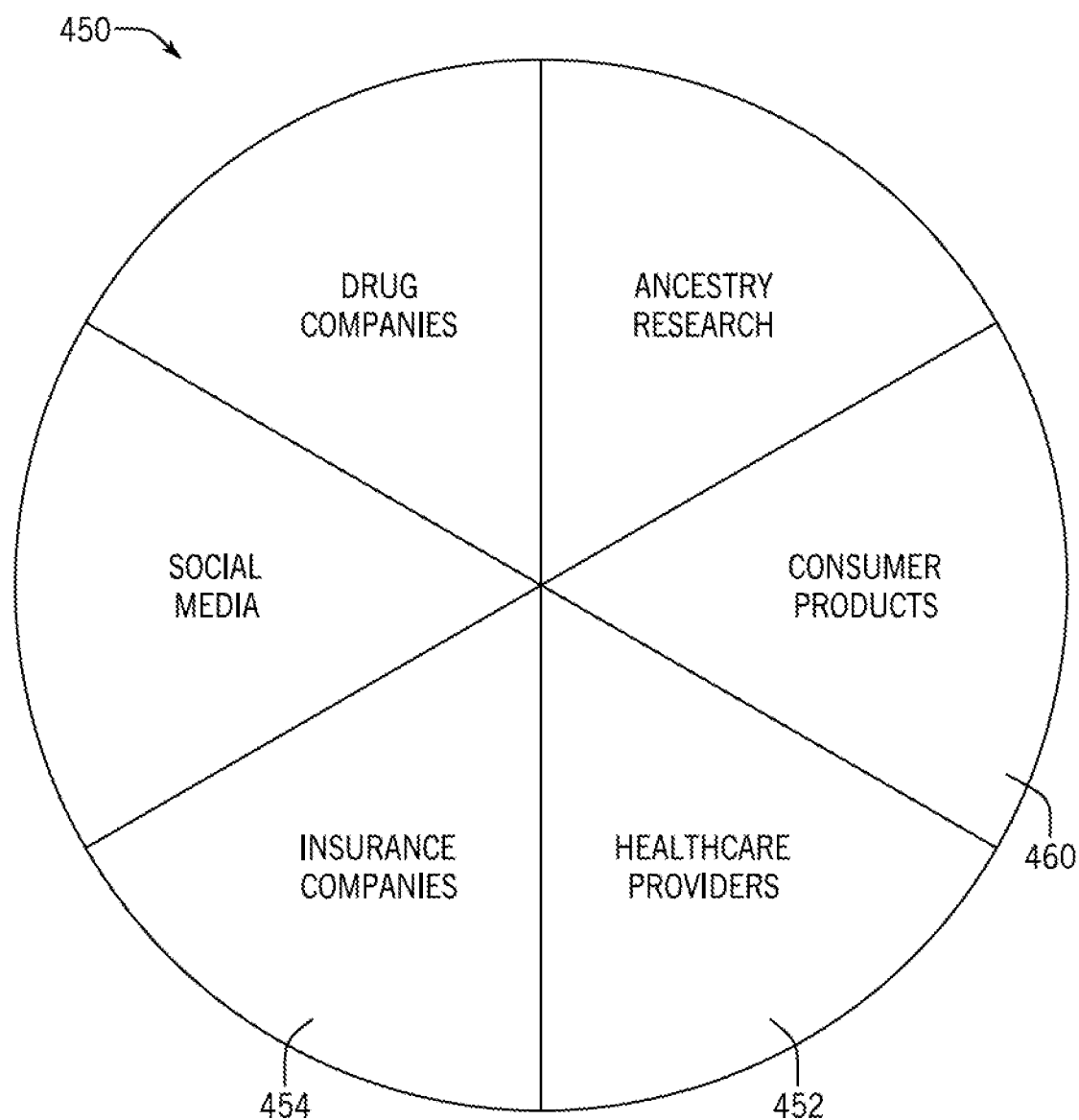
FIG. 11 is an example of display screen showing a genome privacy settings selector for interacting with sequencing data via the hub of the type discussed with reference to FIG. 1.
Figure 12:
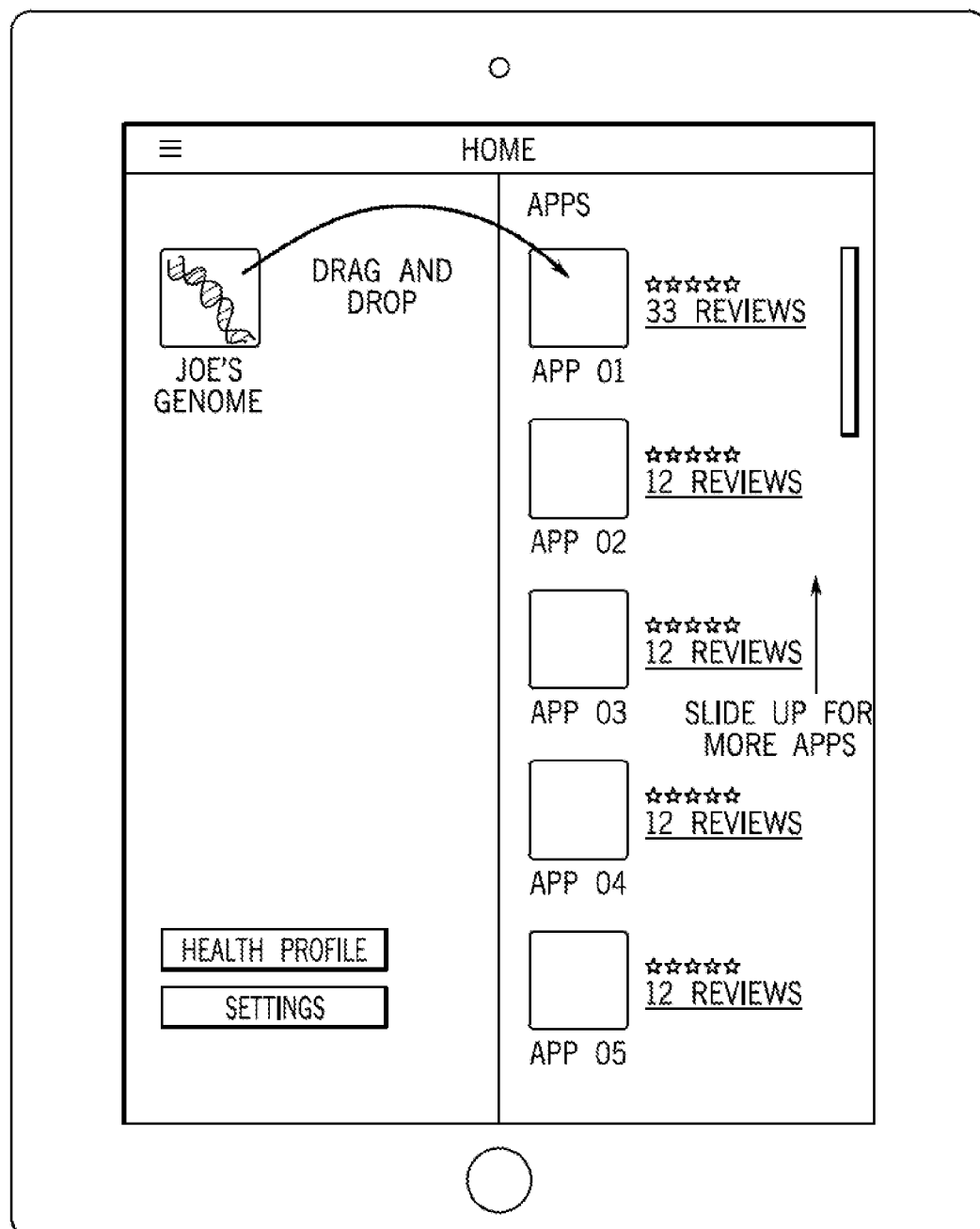
FIG. 12 illustrates a graphical user interface in accordance with some embodiments.
Figure 13:
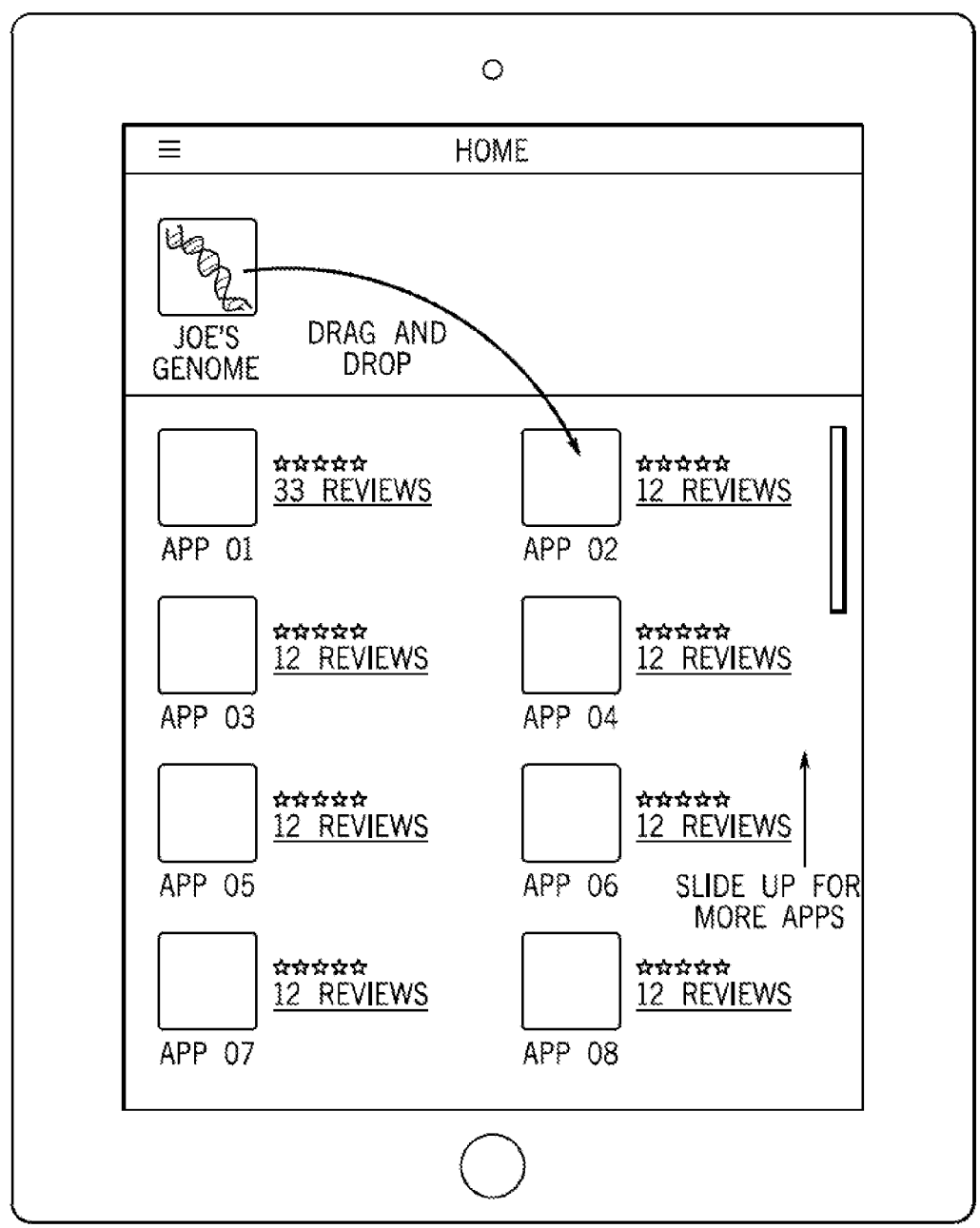
FIG. 13 illustrates a graphical user interface in accordance with some embodiments.
Figure 14:
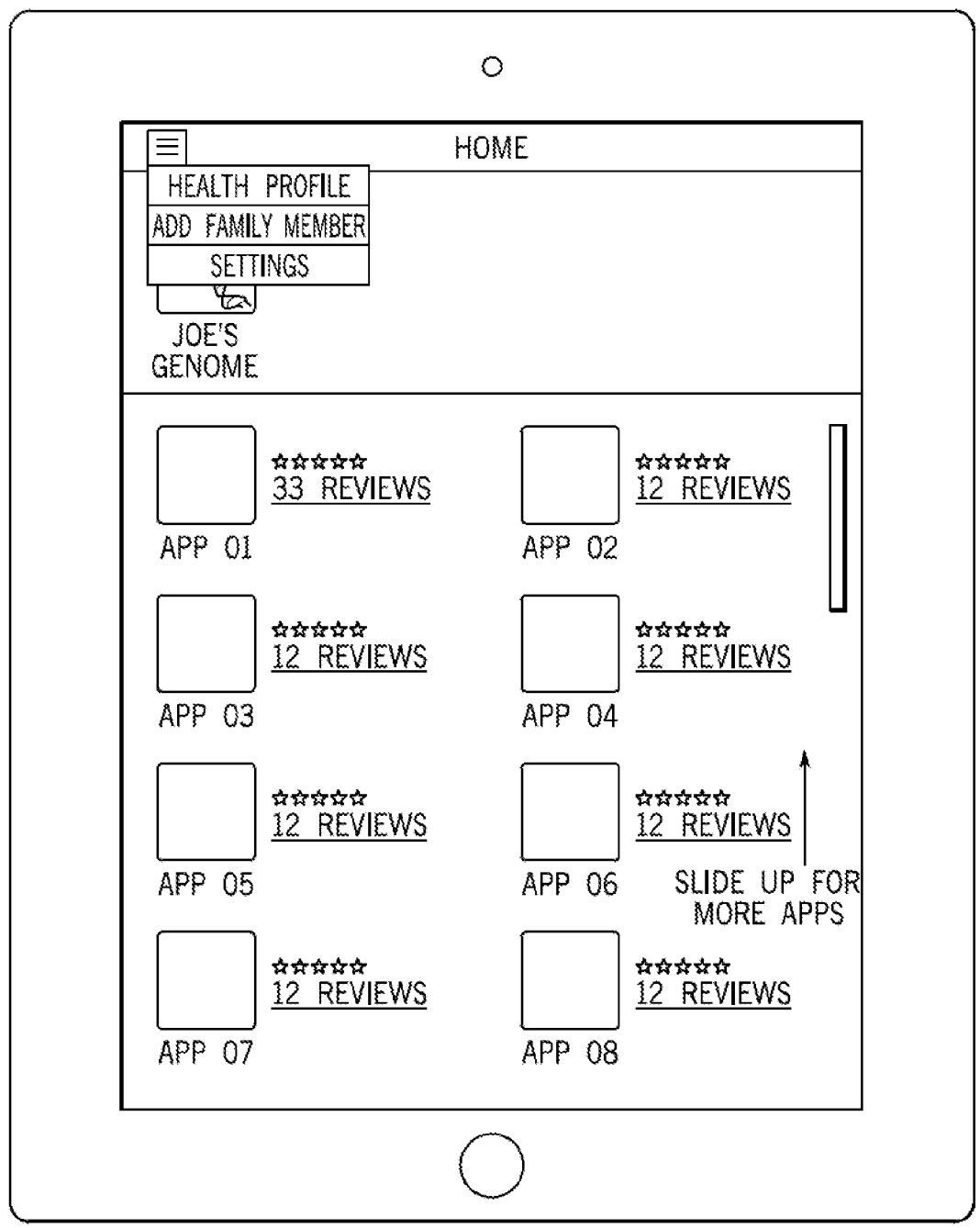
FIG. 14 illustrates a graphical user interface in accordance with some embodiments.
Figure 15:
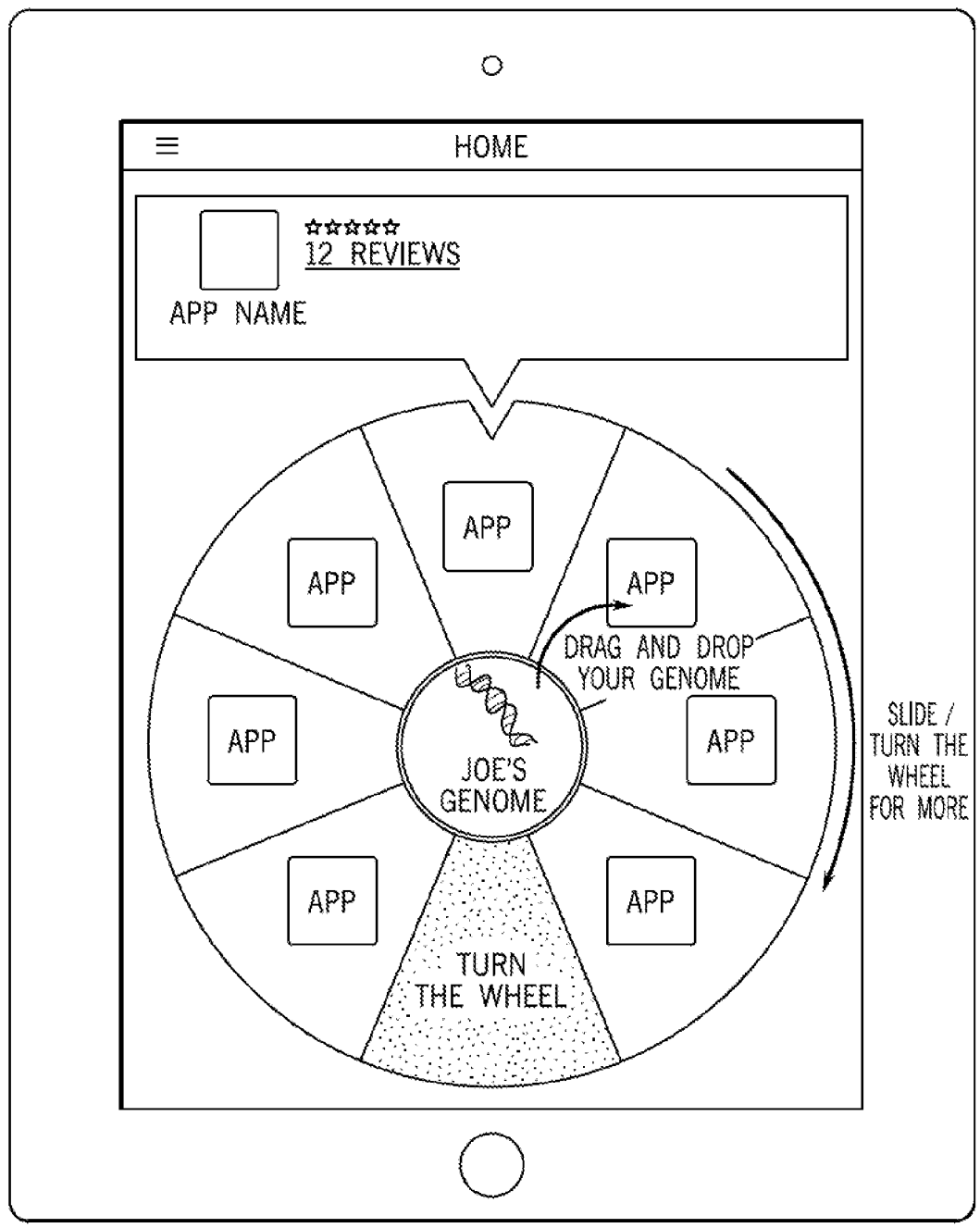
FIG. 15 illustrates a graphical user interface in accordance with some embodiments.

In addition to setting up a user interface, the consumer 20 may interact with the hub 12 in setting data and profile permissions. FIG. 11 is an example of an example of a granular and dynamic permission icon 450. In the depicted embodiment, the granularity may be set at the secondary user level. For example, the icon 450 may be a pie or wheel including selectable regions for specific secondary users 30. By clicking on a particular region, such as "healthcare providers" 452 a list of available permissions and restrictions are displayed. These can be changed or customized depending on the preferences of the consumer 20. The consumer 20 may wish to have open sequence access for certain healthcare providers limited sequence access for insurance companies 454 (e.g., sufficient access to regions of interest to provide documentation for insurance coverage for tests or procedures), and more limited access for consumer product companies 460. To guide the user through various privacy settings, the hub 12 may include stored privacy profiles for example users that are similar to the user configuration profiles in FIG. 10.

Alternatively or additionally, the icon 450 may be configured to facilitate the user selecting sequence chunks for access or permissions. In the case of a whole genome, the icon 450 may be a representation of chromosomes, and the consumer 20 may navigate through the chromosomes to select areas to share with secondary users 30. Accordingly, only certain portions of the sequence data 14 may be shared. In one embodiment, the consumer 20 may share only certain chromosomes, only certain gene sequences, only areas of the genome associated with transcribed genes, only junk DNA, etc. Such sharing may also be granular, and may be customized for individual secondary users 30, as in FIG. 11. Further, the icon 450 may be integrated into the icon 402, so that selecting or dragging the icon 402 also selects the associated permissions. In this manner, the consumer 20 may interact with the hub 12 via a genome avatar or cookie that includes data, profile information, and privacy settings. Further it should be understood that the privacy settings are dynamic, and access to the sequence data 14 may be granted or withheld at any time.

The present disclosure provides a method to present or display a graphical user interface suitable for purchasing, distributing, sharing, displaying, and consuming genomic information. The graphical user interface can be displayed or presented to a user or an individual consumer on a client machine. The client machine may be a mobile device, such as a smart phone, a tablet, or laptop, etc. The client machine may be a non-mobile device, such as a personal desktop computer, among others. In some embodiments, the graphical user interface is displayed or presented on the client machine by an application or program that runs on the client machine. For example, an application on a mobile device may be used to display the graphical user interface to a user.

The graphical user interface is useful for previewing or purchasing genomic products or services in a client-server environment, such as the client communicating to the server through a network connection. The network connection may include the internet, or local intranet, among others.

The graphical user interface is particularly useful for a client-server environment that facilitates the purchase, distribution, display, sharing, and consumption of genomic information. Genomic information is highly personal and confidential, so any transmission of the genomic information between the client and server, or between the client and other clients, should be secure and controlled by the individual consumer. This controlled transmission or distribution of genomic information may make use of encryption or other known security techniques to prevent unauthorized access by third party, such as hackers. User accounts may be created by individual users to facilitate the restriction of unauthorized access to the individual user's genomic information, as well as the limitation or delineation of rights of authorized users. The security techniques, such as encryption and user accounts, restrict access to the genomic information during transmission or download, as well as during storage at a client machine or server. The graphical user interface may also be used by individual users to identify genomic products or services to be purchased from genomic vendors, as well as locate genomic information stored on the client machine, servers of genomic vendors, or other servers.

The present disclosure may be implemented in several ways, such as a method, system, apparatus, graphical user interface, or a computer program product. The computer program product may include machine readable code stored on a computer readable storage medium, such as a hard drive, DVD-ROM, CD-ROM, solid state drive, or any other medium that is capable of storing digital information. These computer readable storage devices need not be physical devices. These computer readable storage devices can also be virtualized storage devices, wherein the logical drives physically reside across multiple machines. The computer program product may also span across geographically diverse locations. For example, the computer program product may include a client machine interface as well as a remote server database that is accessed by the client machine interface.

Certain graphical user interfaces that may be used in conjunction with genomic information are shown in FIGS. 12-15. In a graphical user interface, genomic information may be represented by a genomic representation. For example, a person's whole genome sequence may be represented by an icon in an application window that is generated by an application in a client machine, such as a mobile phone. This icon, or genomic representation, may be used to identify the individual consumer or user to vendors that offer genomic services, such as genealogy. In some embodiments, the genomic representation itself holds the genomic information of the individual consumer. In some embodiments, the genomic representation may be an icon that points to data that is stored in a remote location, such as a server, or locally on the client machine, wherein the data include genomic information. This icon may, in some embodiments, include genotype information, phenotype information, or a combination of genotype and phenotype information. Since the genomic representation and the genomic information that it includes may include private information, security measures, such as encryption, should be used wherever the genomic representation, or genomic information that the genomic representation points to, is stored, as well as the communication involving the genomic representation or genomic information.

In some embodiments, a method to process genomic information includes receiving a sequence of a user's DNA; receiving phenotype information of the user; associating the sequence of the user's DNA with the phenotype information of the user; storing the sequence of the user's DNA and the phenotype information of the user in a central repository; generating an icon in a graphical user interface by an application on a client device; and creating a pointer from the icon to the stored sequence of the user's DNA.

Different vendors may provide different genomic services. One vendor may provide genealogy services, while another vendor may provide health and wellness services. These different services may require different genomic information in order to perform their respective genomic services. For example, Vendor A may require Gene X and Gene Y to provide Services L, while Vendor B may require Gene Z to provide Services M. In this case, an individual user may not want to share his or her genomic information if the genomic information included his or her entire genome sequence. In some embodiments, a graphical user interface will include controls or settings that allow the user to modify the level of sharing and what subsets of his or her genomic information to share.

Following the example above, suppose the user's genomic information included the user's entire genomic sequence, or the user's complete DNA sequence. The user is not comfortable with sharing Genes Y and Z since these genes indicate that the user will likely contract a debilitating disease in his life. By setting the appropriate privacy settings in the graphical user interface, third parties will not be able to view Genes Y and Z of the user. Indeed, as a default setting, it may be desirable that the entire genomic sequence and/or identification information of the user is set to private, meaning that no third party will be able to view the entire genomic sequence or identifying information of the user without first obtaining permission from the user.

Since the user has not shared Genes Y and Z with third parties, and since Vendor A requires Gene Y and Vendor B requires Gene Z, the user will not be able to utilize the services of Vendors A or B. However, in some embodiments, the user may be able to browse the selection of services offered by the vendors even when the required subset of genetic information is not shared. For example, the graphical user interface may include a first application window produced by an application on the client machine that allows the user to browse a number of vendors that provide genomic services, and a second application window produced by the application on the client machine that allows the user to view a number of vendor services provided by a vendor upon selecting the vendor from the number of vendors in the first application window. The content of the first application window, which may include a list of vendors, includes data that may be stored on a remote server. For example, the application may communicate with the remote server via a wireless network connection to determine a list of vendors and display the vendors in the first application window of the graphical user interface. Similarly, the content of the second application window, which may include a list of vendor services or genomic offerings provided by a specific vendor, may be stored on the remote server. For example, the application may communicate with the remote server via a wireless connection to determine a list of genomic offerings and display the genomic offerings in the second application window of the graphical user interface.

In some embodiments, a method to process genomic information includes prompting a user, through a graphical user interface, to select at least a portion of the user's genomic information; upon receiving the selection of at least a portion of the user's genomic information, prompting the user, through the graphical user interface, to indicate a level of sharing for the selection of at least a portion of the user's genomic information; and based on the selection of at least a portion of the user's genomic information and the indicated level of sharing, allowing a second user to view the user's genomic information.

The user may preview, browse or read a brief description of the vendor services presented in the second application window generated by the application. In some embodiments, the preview or brief description of the vendor services may indicate what genomic information, or what genes are required to be shared before the vendor services may be utilized. Such services may include applications for data analysis as well as novelty or entertainment applications, and shopping or vendor applications. For example, the applications may include applications for heath analysis. In another example, the applications may include applications for purchasing consumer goods that are personalized based on the sequence data 14. For example, a consumer could elect to purchase an item of clothing embroidered with specific sequences of their own personal DNA or specific phenotypes, in which case the hub would release those sequences to the consumer good manufacturer to be incorporated in to the personalized product. Examples of such products may include DNA socks, shirts, hats, bags, etc. in addition, the application may include diet or fitness applications. For example, the application may yield dietary personalization and recommendations for restrictions based on the sequence data 14 and analysis of the presence or absence of allergies.

The vendor, or the vendor services, may be represented by vendor icon, or a vendor representation. Following the example above, Vendor A may be displayed as an icon in the graphical user interface. The vendor representation, or vendor icon, may include a graphical representation of the vendor, such as a trademark of the vendor or other identifiable graphic that identifies the vendor. The vendor representation may also include a graphical representation of the vendor services, such as a thumbnail of the product, or a trademark of the product or service.

In some embodiments, a user may drag or drop the genomic representation, or icon, over the vendor representation to determine if the vendor may provide vendor services to the user. For example, a user may drag the user's genomic representation to the vendor representation, and the vendor representation may be grayed out, indicating that the vendor services are not available under the current level of sharing, and a prompt in the graphical user interface may indicate to the user which subset of genomic information is required in order to utilize the vendor services. The prompt may also indicate which subset of genomic information has been shared, and what remaining genomic information needs to be shared. Following the above example, if the vendor is Vendor A, the prompt may indicate to the user that Gene X has been shared, but Gene Y will also need to be shared in order to utilize Service L. In the example of personalization of consumer goods, the prompt may indicate which genes are shared and that are therefore available for using for personalization.

Especially in a small touch screen client machine, such as a mobile device that lacks a hardware keyboard, dragging or dropping a genomic representation entirely onto a vendor representation may be cumbersome. In such cases, it may be desirable to use a pre-determined percentage of overlap to conclude that the user intended to drag the genomic representation onto the vendor representation. For example, if the pre-determined percentage of overlap is 70%, upon the user covering 70% or more of the vendor representation with the genomic information, the application may then prompt the user in the graphical user interface which vendor services, or genomic services provided by a vendor, are available, or what additional genomic information is required before being able to utilize the vendor services of the vendor.

In some embodiments, a method to process genomic information includes dragging, by a user, a genomic representation to a vendor representation in a graphical user interface; upon a pre-determined percentage of the genomic representation overlapping with the vendor representation, determining a vendor-defined dataset, wherein the vendor-defined dataset is defined by a vendor; comparing the vendor-defined data subset to a user-defined dataset; based on the comparison, determining if the vendor-defined dataset is a subset of the user-defined dataset; if the vendor-defined dataset is a subset of the user-defined dataset: displaying genomic offerings from the vendor in the graphical user interface; if the vendor-defined dataset is not a subset of the user-defined dataset: identifying the portions of the vendor-defined dataset that are not a subset of the user-defined dataset; displaying, in the graphical user interface, the vendor-defined dataset that is not a subset of the user-defined dataset.

In some embodiments, it may be advantageous for a central server to store genomic information of a user. This central server, or centralized database, may be spread across diverse geographic regions, such that multiple servers may carry redundant data for data disaster situations or to maintain a higher uptime percentage. The data stored on the central server may be accessed by individual users, or by vendors. For example, if a vendor needed to view a user's genomic information in order to carry out genomic offerings or more personalize the genomic offerings, the vendor would communicate with the central server to access the user's genomic information, assuming the user allowed the vendor to view the user's genomic information.

Similar to how an individual user has a user account, a vendor may have a vendor account. Having a vendor account will allow the central server to authenticate the vendor, and to allow the vendor to access a specific user's genomic information if the specific user communicated with the server that the vendor account is allowed to view the user's genomic information, or a subset thereof. The vendor account also may be used to authenticate the vendor when the vendor wants to add new genomic offerings or vendor services to the vendor account.

An individual user may share his or her genomic information with other individual users. For example, an individual user may share his genomic information with his brother, parents, or close friends—who also have individual user accounts to access an instance of the application on their respective client machines. In this sense, there may be a network of associations, wherein each associate may be given access to a different level or different subset of the individual user's genomic information. For example, the individual user may share his entire DNA sequence with his parents and brother, but only Genes X, Y, and Z with his close friends. Further, the individual user may authorize or increase the level of sharing such that an associate may be allowed to share the individual user's genomic information with other third parties. For example, the individual user may authorize his parents to share the individual user's genomic information with vendors who specialize in comparing multiple genomes and issuing a report on the comparison. Depending on the amount of genomic information shared, personally identifiable information may be redacted from the shared genomic information, such that the vendor would not be able to trace the individual user's genomic information back to the individual user. For example, the individual user's father may submit his own DNA sequence with the individual user's genomic information, but not identify the individual user when submitting the individual user's genomic information. In addition, the individual user's genomic information by itself is not sufficient to identify the individual user. In other words, the individual user's genomic information is a subset of the individual user's complete DNA sequence.

Various levels of sharing may be applied to vendors as well. For example, an individual user may allow a vendor to access and view the individual user's genomic information in the course of providing genomic offerings of vendor services. The individual user may also allow the vendor to indicate to other vendors that the individual user utilized the vendor's genomic offerings. Based on this indication, other vendors may prompt the user through the graphical user interface if the user would be interested in previewing or utilizing the other vendors' genomic offerings or their vendor services.

All of this transaction data, that is, data that contains all the genomic offerings that the individual user utilized or previewed, may be stored in a central server. The central server need not be physically one machine, but may be geographically diverse with multiple machines in different locations. The central server may also include the genomic information of individual users, wherein users access and control their respective genomic information through a graphical user interface generated by an application running on a client machine. With a large number of individual users storing their transaction data and genomic information on the central server, the central server may act as a sort of library. The Library of Genomics may be accessed by various organizations for a wide variety of reasons.

For example, with sufficient permission from individual users, a research institution interested in using population genomes may want to access the Library of Genomics to get a sufficient sample size of the genomes in a specific metropolitan area. The data in the Library of Genomics may be redacted such that personally identifiable information is not disclosed. The Library of Genomics may include user location and user age, among other types of metadata about the user, and associate it with the user's genomic information. Instead of generating a report line by line with each individual user's genomic information with their corresponding name, location, and age, the report may anonymize the data such that no individual can be traced back from the report. For example, the report may include a section such as "All City Residents Age 1-18" and display a list of genomic information or DNA sequences with no other associated metadata, such as name, address, or date of birth.

The Library of Genomics may also be used to determine which genomic offerings or vendor services an individual user may be interested in. Since the Library of Genomics includes transaction data, an application can compare the transaction data of one user with the transaction data of a second user. For example, suppose User A browsed through Vendor 1's genomic offerings through the graphical user interface produced by an application on User A's client machine, and then later viewed Vendor 2's genomic offerings and purchased Service L from Vendor 2. If User B browsed through Vendor 1's genomic offerings through the graphical user interface produced by the application on User B's client machine, and later closed the window displaying Vendor 1's genomic offerings, upon User B's next logging on to the application, the application may push a notification to User B indicating that User B may be interested in Service L from Vendor 2.

In some embodiments, a method to process genomic information may include storing a first user transaction data in a central repository, wherein the first user transaction data is created as the first user completes a first user transaction, wherein the first user transaction includes at least one from the following: view a vendor, view a vendor offering, and purchase a vendor offering; storing a second user transaction data in a central repository, wherein the second user transaction data is created as the second user completes a second user transaction, wherein the first user transaction includes at least one from the following: view a vendor, view a vendor offering, and purchase a vendor offering; comparing the first user transaction data to the second user transaction data; pushing a notification to the second user in a graphical user interface with a vendor offering based on the comparison.

The Library of Genomics and the graphical user interface used to access the Library of Genomics may, in some embodiments, be part of a Genomics Environment. The Genomics Environment is a platform that allows third parties to publish applications that utilize the graphical user interface, as well as the information included in the Library of Genomics. For example, Company A may house the Library of Genomics and allow individual users to access the Library of Genomics and the Genomics Environment through a graphical user interface. Company A may also publish an API kit, or an application programming interface kit for the Genomics Environment that allows Company B to publish an application that Company B created on the Genomics Environment. Company A may impose some restrictions on Company B's application, such as security requirements, content requirements, and privacy requirements, among others before allowing Company B's application to be published on the Genomics Environment. After being published on the Genomics Environment, individual users will be able to download, install, or otherwise utilize Company B's application through the Genomics Environment and graphical user interface. However, if Company B's application requires sensitive or otherwise unshared genomic information of an individual user that is stored in the Library of Genomics, the application may not work correctly, or the genomic offerings may not be fully utilized. The individual user may decide to share his or her respective genomic information with Company B's application if the individual user decides to do so. If not, the individual user may delete the program, or otherwise not utilize Company B's application. Ideally, before download, install, or utilization by an individual user, Company B's application should indicate which genomic information is required for Company B's application to be fully utilized.

When an individual user first joints the Genomics Environment, the individual user may have no individual user genomic information. In some embodiments, a vendor that is participating in the Genomics Environment may offer a genomic offering that includes whole genome sequencing. The individual user may then utilize the vendor's genomic offering, such as ordering a kit to return a DNA sample. In some embodiments, the company hosting the Genomics Environment may provide the genome sequencing service. In some embodiments, the process of opening a new user account to join the Genomics Environment may include sending a DNA sample to the company in charge of the Genomics Environment.

Other aspects and advantages of the disclosure will become apparent from this detailed description taken in conjunction with the accompanying drawings which illustrate, by way of example, the principles of the disclosure.

What is claimed is:

1. A computer-implemented method for processing genomic information, the method comprising:
   providing a graphical user interface including a user icon and at least one third party icon of a third-party application, the graphical user interface being configured to accept dragging input by a user from the user icon to the at least one third-party icon-, the user icon linked to a database that stores an available genomic sequence range of the user and at least one set of privileges for the genomic information of the user;
   accessing from the database, using a microprocessor, a user-defined genomic sequence dataset that includes genomic sequence data including the available genomic sequence range that is available for the user according to the at least one set of privacy settings associated with the user, wherein the user-defined dataset is determined based on a level of sharing of genomic information defined by the user;
   displaying, using a microprocessor, custom genomic offering options according to the privacy settings of the genomic sequence data directly built into the graphical user interface by:
   i) upon a pre-determined percentage of the user icon being dragged to overlap with one of the at least one third-party icon, accessing a third-party-defined dataset of the one third party icon, using a microprocessor, wherein the third-party-defined dataset comprises at least one required genomic sequence region that is defined by the corresponding third-party of the third-party icon, wherein the at least one required genomic sequence region comprises a region of nucleotide sequences associated with one or more genes;
   ii) computationally comparing genomic positions of each nucleotide of the at least one required genomic sequence region of the third-party-defined dataset to the genomic sequence data of the user-defined genomic sequence dataset;
   iii) determining whether the at least one required genomic sequence region of the third-party-defined dataset covers the genomic sequence data of the user-defined dataset based on the third-party genomic positions of each nucleotide of the at least one required genomic sequence region falling within the user genomic positions of the available genomic sequence range of the genomic sequence data;
   iv) when the at least one required genomic sequence region of the third-party-defined dataset covers the genomic sequence data of the user-defined dataset:
   displaying genomic offerings from the third-party in the graphical user interface; and
   transmitting required genome sequence information from the user-defined dataset to a genomic offering on the third-party application based on user input; and
   v) when the at least one required genomic sequence region of the third-party-defined dataset does not cover the genomic sequence data of the user-defined dataset:
   identifying the genomic positions of the at least one required genomic sequence region of the third-party-defined dataset that do not cover the genomic sequence data of the user-defined dataset;
   preventing transmission of genome sequence information from the user-defined dataset to the genomic offerings of the third-party application; and
   displaying, in the graphical user interface, the genomic positions of the at least one required genomic sequence region of the third-party-defined dataset that do not cover the genomic sequence data of the user-defined dataset.

2. The method as recited in claim 1, wherein the user-defined dataset comprises less than an entire genomic sequence.

3. The method as recited in claim 1, wherein the user-defined dataset comprises anonymized genomic information without identification information of the user.

4. The method as recited in claim 1, wherein the user icon is a genome icon representing an entire genome of the user.

5. The method as recited in claim 4, wherein the third-party icon comprises a third-party application icon, and wherein the overlapping with the third-party icon comprises overlapping of the user icon with the third-party application icon.

6. The method as recited in claim 1, wherein displaying the genomic positions of the at least one required genomic sequence region of the third-party-defined dataset comprises displaying information related to one or more genes that are required to use a vendor service.

7. The method as recited in claim 1, further comprising displaying a prompt to the user to share the third-party-defined dataset that does not cover the genomic sequence data of the user-defined dataset to use a vendor service.

8. The method as recited in claim 1, further comprising displaying a list of services available from other third parties based on the user-defined dataset.

9. The method as recited in claim 1, further comprising displaying a prompt to the user to obtain new or additional genome information within the third-party-defined dataset.

10. The method as recited in claim 1, wherein the predetermined percentage is less than 100%.

11. A system for processing genomic information, the system comprising a microprocessor configured to:
    accept input from a user to drag a user icon to a third-party icon of a third-party application in a graphical user interface, the user icon representing genomic information of the user, the user icon linked to a database that stores an available genomic sequence range of the user and at least one set of privileges for the genomic information of the user;
    access from the database a user-defined genomic sequence dataset that includes genomic sequence data including the available genomic sequence range that is available for the user according to the at least one set of privacy settings associated with the user wherein the user-defined dataset is determined based on a level of sharing of genomic information defined by the user;
    displaying, using a microprocessor, custom genomic offering options according to the privacy settings of the genomic sequence data directly built into the graphical user interface by:
    (i) upon a pre-determined percentage of the user icon being dragged to overlap with one of the at least one third-party icon, accessing a third-party-defined dataset of the one third party icon, wherein the third-party-defined dataset comprises at least one required genomic sequence region that is defined by the corresponding third-party of the third-party icon, wherein the at least one required genomic sequence region comprises nucleotide sequences associated with one or more genes;

(ii) computationally compare genomic positions of each nucleotide of the at least one required genomic sequence region of the third-party-defined dataset to the genomic sequence data of the user-defined genomic sequence dataset;

(iii) determine whether the at least one required genomic sequence region of the third-party-defined dataset covers the genomic sequence data of the user-defined dataset based on the third-party genomic position of each nucleotide of the at least one required genomic sequence region falling within the user genomic positions of the available genomic sequence range of the sequence data;

(iv) when the at least one required genomic sequence region of the third-party-defined dataset covers the genomic sequence data of the user-defined dataset:
  display genomic offerings from the third-party in the graphical user interface; and
  transmitting required genome sequence information from the user-defined dataset to a genomic offering on the third-party application based on user input; and (v) when the at least one required genomic sequence region of the third-party-defined dataset does not cover the genomic sequence data of the user-defined dataset:
  identify the genomic positions of the at least one required genomic sequence region of the third-party-defined dataset does not cover the genomic sequence data of the user-defined dataset;
  preventing transmission of genome sequence information from the user-defined dataset to the genomic offerings of the third-party application; and
  display, in the graphical user interface, the genomic positions of the at least one required genomic sequence region of the third-party-defined dataset that do not cover the user-defined dataset.

12. The system as recited in claim 11, wherein the processor is configured to receive a user input related to the genomic offerings and to access the user-defined dataset from a memory based on the user input.

13. The system as recited in claim 11, wherein the processor is configured to receive a user input related to the genomic offerings and provide instructions to a remote device to access the user-defined dataset based on the user input.

14. The system as recited in claim 11, wherein, when the at least one required genomic sequence region of the third-party-defined dataset does not cover the genomic sequence data of the third-party-defined dataset, the processor is configured to provide instructions to display the third-party icon with a different graphical characteristic relative to when the at least one required genomic sequence region of the third-party-defined dataset does cover the genomic sequence data of the third-party-defined dataset.

15. The system as recited in claim 11, wherein the user-defined dataset comprises less than an entire genomic sequence of the user.

16. The system as recited in claim 11, wherein the user-defined dataset comprises user identification or phenotype information.

17. The system as recited in claim 11, wherein the predetermined percentage is less than 100%.

* * * * *